(12) United States Patent
Gillespie et al.

(10) Patent No.: US 12,138,460 B2
(45) Date of Patent: *Nov. 12, 2024

(54) AUTOMATED PROGRAM OPTIMIZATION

(71) Applicant: Boston Scientific Neuromodulation Corporation, Valencia, CA (US)

(72) Inventors: Christopher Ewan Gillespie, Stevenson Ranch, CA (US); Michael A. Moffitt, Solon, OH (US); Que T. Doan, West Hills, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 18/084,918

(22) Filed: Dec. 20, 2022

(65) Prior Publication Data
US 2023/0123406 A1    Apr. 20, 2023

Related U.S. Application Data

(63) Continuation of application No. 16/884,361, filed on May 27, 2020, now Pat. No. 11,565,114, which is a
(Continued)

(51) Int. Cl.
*A61N 1/36* (2006.01)
*A61N 1/372* (2006.01)

(52) U.S. Cl.
CPC ..... *A61N 1/36146* (2013.01); *A61N 1/36025* (2013.01); *A61N 1/36071* (2013.01);
(Continued)

(58) Field of Classification Search
None
See application file for complete search history.

(56) References Cited

U.S. PATENT DOCUMENTS 6,934,580 B1    8/2005   Osorio et al.
7,184,837 B2    2/2007   Goetz
(Continued)

FOREIGN PATENT DOCUMENTS

CN    103249453 A    8/2013
CN    108348750 A    7/2018
(Continued)

OTHER PUBLICATIONS

"U.S. Appl. No. 15/269,674, Advisory Action mailed Jan. 10, 2020", 6 pgs.
(Continued)

*Primary Examiner* — Carl H Layno
*Assistant Examiner* — Manolis Pahakis
(74) *Attorney, Agent, or Firm* — Schwegman Lundberg & Woessner, P.A.

(57) ABSTRACT

An example of a system may include a processor and a memory device comprising instructions, which when executed by the processor, cause the processor to access at least one of: patient input, clinician input, or automatic input, use the patient input, clinician input, or automatic input in a search method. The search method may be designed to evaluate a plurality of candidate neuromodulation parameter sets to identify an optimal neuromodulation parameter set and to program a neuromodulator using the optimal neuromodulation parameter set to stimulate a patient.

20 Claims, 13 Drawing Sheets

Related U.S. Application Data continuation of application No. 15/269,674, filed on Sep. 19, 2016, now abandoned.

(60) Provisional application No. 62/221,335, filed on Sep. 21, 2015.

(52) U.S. Cl.
CPC ..... *A61N 1/36139* (2013.01); *A61N 1/37247* (2013.01); *A61N 1/37264* (2013.01)

(56) References Cited

U.S. PATENT DOCUMENTS

| | | |
|---|---|---|
| 7,209,787 B2 | 4/2007 | Dilorenzo |
| 7,231,253 B2 | 6/2007 | Tidemand et al. |
| 7,231,254 B2 | 6/2007 | Dilorenzo |
| 7,239,926 B2 | 7/2007 | Goetz |
| 7,252,090 B2 | 8/2007 | Goetz |
| 7,657,317 B2 | 2/2010 | Thacker et al. |
| 9,211,417 B2 | 12/2015 | Heldman et al. |
| 9,238,142 B2 | 1/2016 | Heldman et al. |
| 9,517,344 B1 | 12/2016 | Bradley |
| 9,713,722 B1 | 7/2017 | Astrom et al. |
| 10,124,173 B2 | 11/2018 | Bonnet et al. |
| 10,744,328 B2 | 8/2020 | Grill et al. |
| 10,842,997 B2 | 11/2020 | Moffitt et al. |
| 2004/0111127 A1 | 6/2004 | Gliner |
| 2004/0131998 A1 | 7/2004 | Marom et al. |
| 2005/0075669 A1 | 4/2005 | King |
| 2006/0241722 A1 | 10/2006 | Thacker et al. |
| 2007/0032834 A1 | 2/2007 | Gliner et al. |
| 2007/0100392 A1 | 5/2007 | Maschino et al. |
| 2008/0004674 A1 | 1/2008 | King et al. |
| 2008/0027514 A1 | 1/2008 | DeMulling et al. |
| 2008/0097553 A1 | 4/2008 | John |
| 2009/0118786 A1 | 5/2009 | Meadows et al. |
| 2009/0234419 A1 | 9/2009 | Maschino et al. |
| 2009/0281594 A1 | 11/2009 | King et al. |
| 2009/0287271 A1 | 11/2009 | Blum et al. |
| 2010/0205541 A1 | 8/2010 | Rapaport et al. |
| 2010/0228314 A1 | 9/2010 | Goetz |
| 2011/0208012 A1 | 8/2011 | Gerber et al. |
| 2012/0014580 A1 | 1/2012 | Blum et al. |
| 2012/0016435 A1 | 1/2012 | Rom |
| 2012/0271374 A1 | 10/2012 | Nelson et al. |
| 2013/0023950 A1 | 1/2013 | Gauthier |
| 2013/0123684 A1 | 5/2013 | Giuffrida et al. |
| 2014/0005743 A1 | 1/2014 | Giuffrida et al. |
| 2014/0067016 A1 | 3/2014 | Kaula et al. |
| 2014/0074179 A1 | 3/2014 | Heldman et al. |
| 2014/0074180 A1 | 3/2014 | Heldman et al. |
| 2014/0163640 A1 | 6/2014 | Edgerton et al. |
| 2014/0277267 A1 | 9/2014 | Vansickle et al. |
| 2014/0277278 A1 | 9/2014 | Keel et al. |
| 2014/0350634 A1 | 11/2014 | Grill et al. |
| 2014/0364920 A1 | 12/2014 | Doan et al. |
| 2015/0005680 A1 | 1/2015 | Lipani |
| 2015/0039047 A1 | 2/2015 | Parker |
| 2015/0066104 A1 | 3/2015 | Wingeier et al. |
| 2015/0165202 A1 | 6/2015 | Grandhe |
| 2015/0165209 A1 | 6/2015 | Grandhe et al. |
| 2015/0217116 A1 | 8/2015 | Parramon et al. |
| 2015/0231396 A1 | 8/2015 | Burdick et al. |
| 2015/0238762 A1 | 8/2015 | Pal et al. |
| 2016/0008632 A1 | 1/2016 | Wetmore et al. |
| 2016/0144186 A1 | 5/2016 | Kaemmerer et al. |
| 2017/0043167 A1 | 2/2017 | Widge et al. |
| 2017/0056642 A1 | 3/2017 | Moffitt et al. |
| 2017/0080234 A1 | 3/2017 | Gillespie et al. |
| 2017/0095667 A1 | 4/2017 | Yakovlev et al. |
| 2017/0147722 A1 | 5/2017 | Greenwood |
| 2017/0173335 A1 | 6/2017 | Min et al. |
| 2017/0197086 A1 | 7/2017 | Howard et al. |
| 2017/0258352 A1 | 9/2017 | Wood et al. |
| 2017/0304625 A1 | 10/2017 | Buschman |
| 2017/0325700 A1 | 11/2017 | Lane et al. |
| 2019/0321583 A1 | 10/2019 | Poltorak |
| 2020/0117900 A1 | 4/2020 | Deng et al. |
| 2020/0353264 A1 | 11/2020 | Gillespie et al. |
| 2020/0376272 A1 | 12/2020 | Block et al. |
| 2021/0125502 A1 | 4/2021 | Mansor et al. |
| 2021/0383201 A1 | 12/2021 | Gu |
| 2022/0189185 A1 | 6/2022 | Wyss et al. |
| 2022/0198245 A1 | 6/2022 | Cleland et al. |

FOREIGN PATENT DOCUMENTS

| | | |
|---|---|---|
| CN | 108348750 B | 3/2022 |
| EP | 3352844 B1 | 4/2020 |
| WO | WO-2017053237 A1 | 3/2017 |

OTHER PUBLICATIONS

"U.S. Appl. No. 15/269,674, Final Office Action mailed May 18, 2018", 13 pgs.

"U.S. Appl. No. 15/269,674, Final Office Action mailed Sep. 27, 2019", 12 pgs.

"U.S. Appl. No. 15/269,674, Non Final Office Action mailed Feb. 15, 2019", 10 pgs.

"U.S. Appl. No. 15/269,674, Non Final Office Action mailed Oct. 5, 2017", 10 pgs.

"U.S. Appl. No. 15/269,674, Response filed Oct. 15, 2018 to Final Office Action mailed May 18, 2018", 12 pgs.

"U.S. Appl. No. 15/269,674, Response filed Nov. 26, 2019 to Final Office Action mailed Sep. 27, 2019", 11 pgs.

"U.S. Appl. No. 15/269,674, Response filed Dec. 20, 2017 to Non Final Office Action mailed Oct. 5, 2017", 9 pgs.

"U.S. Appl. No. 15/269,674, Response filed Jun. 3, 2019 to Non-Final Office Action mailed Feb. 15, 2019", 9 pgs.

"U.S. Appl. No. 16/884,361 Prelimianry Amendment filed Aug. 4, 2020", 8 pgs.

"U.S. Appl. No. 16/884,361, Advisory Action mailed Jan. 12, 2022", 5 pgs.

"U.S. Appl. No. 16/884,361, Examiner Interview Summary mailed Aug. 22, 2022", 2 pgs.

"U.S. Appl. No. 16/884,361, Final Office Action mailed Jul. 23, 2021", 14 pgs.

"U.S. Appl. No. 16/884,361, Non Final Office Action mailed Feb. 5, 2021", 13 pgs.

"U.S. Appl. No. 16/884,361, Non Final Office Action mailed Apr. 20, 2022", 28 pgs.

"U.S. Appl. No. 16/884,361, Notice of Allowance mailed Sep. 6, 2022", 10 pgs.

"U.S. Appl. No. 16/884,361, Response filed Jan. 19, 2022 to Advisory Action mailed Jan. 12, 2022", 15 pgs.

"U.S. Appl. No. 16/884,361, Response filed Apr. 21, 2021 to Non Final Office Action mailed Feb. 5, 2021", 11 pgs.

"U.S. Appl. No. 16/884,361, Response filed Aug. 17, 2022 to Non Final Office Action mailed Apr. 20, 2022", 11 pgs.

"U.S. Appl. No. 16/884,361, Response filed Sep. 23, 2021 to Final Office Action mailed Jul. 23, 2021", 13 pgs.

"Australian Application Serial No. 2016325450, First Examination Report mailed Jul. 11, 2018", 3 pgs.

"Chinese Application Serial No. 201680066756.3, Office Action mailed Dec. 22, 2020", w/English translation, 25 pgs.

"Chinese Application Serial No. 201680066756.3, Response filed Apr. 30, 2021 to Office Action mailed Dec. 22, 2020", w/ English Claims, 14 pgs.

"European Application Serial No. 16774765.8, Response filed Nov. 21, 2018 to Communication Pursuant to Rules 161 and 162 EPC mailed May 11, 2018", 16 pgs.

"International Application Serial No. PCT/US2016/052510, International Preliminary Report on Patentability mailed Apr. 5, 2018", 6 pgs.

"International Application Serial No. PCT/US2016/052510, International Search Report mailed Jan. 2, 2017", 4 pgs.

"International Application Serial No. PCT/US2016/052510, Written Opinion mailed Jan. 2, 2017", 4 pgs.

(56) References Cited

OTHER PUBLICATIONS

"Chinese Application Serial No. 201680066756.3, Office Action mailed Aug. 17, 2021", with English claims, 8 pgs.

AUTOMATED PROGRAM OPTIMIZATION

CLAIM OF PRIORITY

This application is a continuation of U.S. application Ser. No. 16/884,361, filed May 27, 2020, now issued as U.S. Pat. No. 11,565,114, which is a continuation of U.S. application Ser. No. 15/269,674, filed Sep. 19, 2016, which claims the benefit of priority under 35 U.S.C. § 119(e) of U.S. Provisional Patent Application Ser. No. 62/221,335, filed on Sep. 21, 2015, each of which is herein incorporated by reference in its entirety.

TECHNICAL FIELD

This document relates generally to medical devices, and more particularly, to systems, devices, and methods for delivering neural modulation.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

The neurostimulation energy may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc.

Recent research has shown that the efficacy and efficiency of certain neurostimulation therapies can be improved, and their side-effects can be reduced, by using patterns of neurostimulation pulses that emulate natural patterns of neural signals observed in the human body.

SUMMARY

Example 1 includes subject matter (such as a device, apparatus, or machine) comprising: a processor; and a memory device comprising instructions, which when executed by the processor, cause the processor to: access at least one of: patient input, clinician input, or automatic input; use the patient input, clinician input, or automatic input in a search method, the search method designed to evaluate a plurality of candidate neuromodulation parameter sets to identify an optimal neuromodulation parameter set of the plurality of candidate neuromodulation parameter sets; and program a neuromodulator using the optimal neuromodulation parameter set to stimulate a patient.

In Example 2, the subject matter of Example 1 may include, wherein the patient input comprises subjective data.

In Example 3, the subject matter of any one of Examples 1 to 2 may include, wherein the subjective data comprises a visual analog scale (VAS), numerical rating scale (NRS), a satisfaction score, a global impression of change, or an activity level.

In Example 4, the subject matter of any one of Examples 1 to 3 may include, wherein the clinician input comprises a selected neuromodulation parameter set, a selected neuromodulation parameter set dimension, or a search method configuration option.

In Example 5, the subject matter of any one of Examples 1 to 4 may include, wherein the selected neuromodulation parameter set dimension comprises a spatial location, a frequency, a pulse width, a number of pulses within a burst or train of pulses, the train-to-train interval, the burst frequency of these trains, a pulse duty cycle, or a burst duty cycle.

In Example 6, the subject matter of any one of Examples 1 to 5 may include, wherein the search method configuration option comprises a test range for a neuromodulation parameter set dimension, a termination criteria for a neuromodulation parameter set test, an amount of time to test a neuromodulation parameter set, a minimum evaluation time for a candidate neuromodulation parameter set, or a survival threshold for a neuromodulation parameter set under test.

In Example 7, the subject matter of any one of Examples 1 to 6 may include, wherein the automatic input comprises data received from a patient device.

In Example 8, the subject matter of any one of Examples 1 to 7 may include, wherein the patient device comprises an accelerometer and the automatic input comprises activity data.

In Example 9, the subject matter of any one of Examples 1 to 8 may include, wherein the patient device comprises a heart rate monitor and the automatic input comprises heart rate or heart rate variability.

In Example 10, the subject matter of any one of Examples 1 to 9 may include, wherein the patient device comprises an implantable pulse generator and the automatic input comprises field potentials.

In Example 11, the subject matter of any one of Examples 1 to 10 may include, wherein the search method comprises a sorting algorithm that uses scoring from the patient to sort the plurality of candidate parameter sets and remove parameter sets from the plurality of candidate parameter sets that fail to meet a threshold score.

In Example 12, the subject matter of any one of Examples 1 to 11 may include, wherein the search method comprises a gradient descent system that progresses through the plurality of candidate parameter sets to optimize a dimension of the candidate parameter sets.

In Example 13, the subject matter of any one of Examples 1 to 12 may include, wherein the search method comprises a sensitivity analysis that builds a model from stimulation variables and outcome variables, and uses a regression model to identify a vector of coefficients.

Example 14 includes a machine-readable medium including instructions, which when executed by a machine, cause the machine to perform operations of any of the claims 1-13.

Example 16 includes subject matter (such as a device, apparatus, or machine) comprising: a processor; and a memory device comprising instructions, which when executed by the processor, cause the processor to: access at least one of: patient input, clinician input, or automatic input; use the patient input, clinician input, or automatic input in a search method, the search method designed to evaluate a plurality of candidate neuromodulation parameter sets to identify an optimal neuromodulation parameter set of the plurality of candidate neuromodulation parameter sets; and program a neuromodulator using the optimal neuromodulation parameter set to stimulate a patient.

In Example 17, the subject matter of Example 16 may include, wherein the patient input comprises subjective data.

In Example 18, the subject matter of any one of Examples 16 to 17 may include, wherein the subjective data comprises a visual analog scale (VAS), numerical rating scale (NRS), a satisfaction score, a global impression of change, or an activity level.

In Example 19, the subject matter of any one of Examples 16 to 18 may include, wherein the clinician input comprises a selected neuromodulation parameter set, a selected neuromodulation parameter set dimension, or a search method configuration option.

In Example 20, the subject matter of any one of Examples 16 to 19 may include, wherein the selected neuromodulation parameter set dimension comprises a spatial location, a frequency, a pulse width, a number of pulses within a burst or train of pulses, the train-to-train interval, the burst frequency of these trains, a pulse duty cycle, or a burst duty cycle.

In Example 21, the subject matter of any one of Examples 16 to 20 may include, wherein the search method configuration option comprises a test range for a neuromodulation parameter set dimension, a termination criteria for a neuromodulation parameter set test, an amount of time to test a neuromodulation parameter set, a minimum evaluation time for a candidate neuromodulation parameter set, or a survival threshold for a neuromodulation parameter set under test.

In Example 22, the subject matter of any one of Examples 16 to 21 may include, wherein the automatic input comprises data received from a patient device.

In Example 23, the subject matter of any one of Examples 16 to 22 may include, wherein the patient device comprises an accelerometer and the automatic input comprises activity data.

In Example 24, the subject matter of any one of Examples 16 to 23 may include, wherein the patient device comprises a heart rate monitor and the automatic input comprises heart rate or heart rate variability.

In Example 25, the subject matter of any one of Examples 16 to 24 may include, wherein the patient device comprises an implantable pulse generator and the automatic input comprises field potentials.

In Example 26, the subject matter of any one of Examples 16 to 25 may include, wherein the search method comprises a sorting algorithm that uses scoring from the patient to sort the plurality of candidate parameter sets and remove parameter sets from the plurality of candidate parameter sets that fail to meet a threshold score.

In Example 27, the subject matter of any one of Examples 16 to 26 may include, wherein the search method comprises a gradient descent system that progresses through the plurality of candidate parameter sets to optimize a dimension of the candidate parameter sets.

In Example 28, the subject matter of any one of Examples 16 to 27 may include, wherein the search method comprises a sensitivity analysis that builds a model from stimulation variables and outcome variables, and uses a regression model to identify a vector of coefficients.

Example 29 includes subject matter (such as a method, means for performing acts, machine readable medium including instructions that when performed by a machine cause the machine to performs acts, or an apparatus to perform) comprising: accessing, at a computerized system, at least one of: patient input, clinician input, or automatic input; using the patient input, clinician input, or automatic input in a search method, the search method designed to evaluate a plurality of candidate neuromodulation parameter sets to identify an optimal neuromodulation parameter set of the plurality of candidate neuromodulation parameter sets; and programming a neuromodulator using the optimal neuromodulation parameter set to stimulate a patient.

In Example 30, the subject matter of Example 29 may include, wherein the patient input comprises subjective data, the subjective data a visual analog scale (VAS), numerical rating scale (NRS), a satisfaction score, a global impression of change, or an activity level.

In Example 31, the subject matter of any one of Examples 29 to 30 may include, wherein the clinician input comprises a selected neuromodulation parameter set, a selected neuromodulation parameter set dimension, or a search method configuration option.

In Example 32, the subject matter of any one of Examples 29 to 31 may include, wherein the search method comprises a sorting algorithm that uses scoring from the patient to sort the plurality of candidate parameter sets and remove parameter sets from the plurality of candidate parameter sets that fail to meet a threshold score.

Example 35 includes subject matter (such as a computer-readable medium) comprising: access at least one of: patient input, clinician input, or automatic input; use the patient input, clinician input, or automatic input in a search method, the search method designed to evaluate a plurality of candidate neuromodulation parameter sets to identify an optimal neuromodulation parameter set of the plurality of candidate neuromodulation parameter sets; and program a neuromodulator using the optimal neuromodulation parameter set to stimulate a patient.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
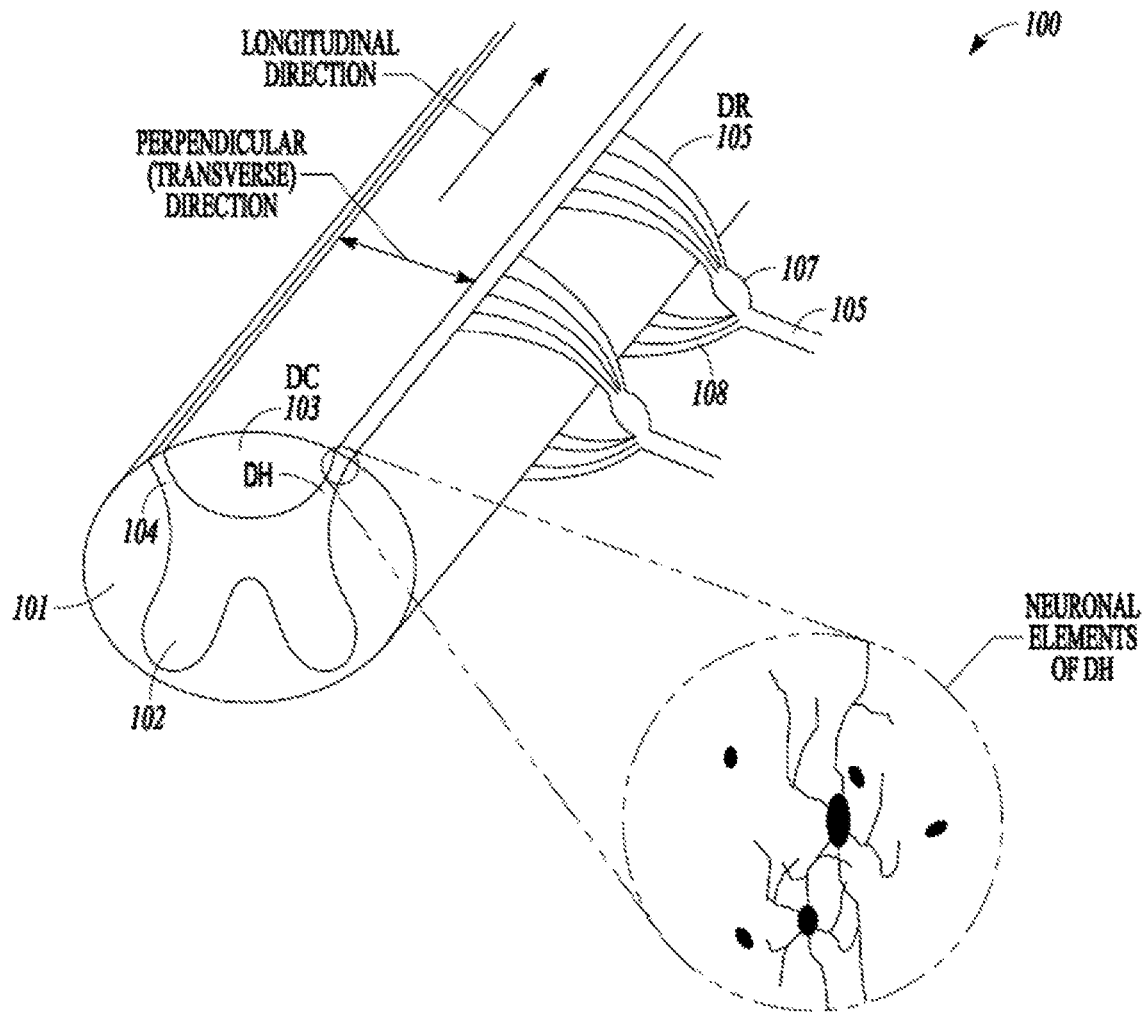
FIG. 1 illustrates a portion of a spinal cord.

Various embodiments described herein involve spinal cord modulation. A brief description of the physiology of the spinal cord and related apparatus is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies standard SCS therapy. Some embodiments deliver therapy where the delivery of energy is perceptible due to sensations such as paresthesia. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1500 Hz or above) of the spinal cord that effectively blocks the transmission of pain signals in the afferent fibers in the DC. Some embodiments herein selectively modulate DH tissue or DR tissue over DC tissue to provide sub-perception therapy. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

Figure 2:
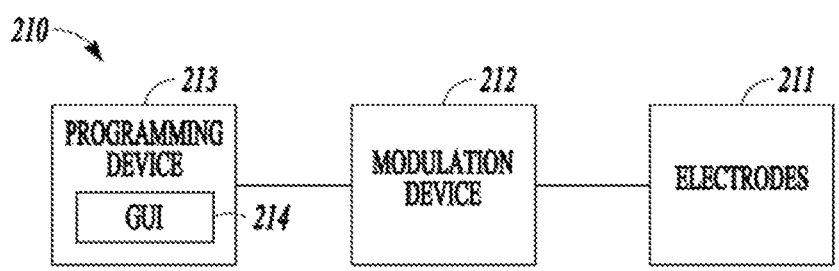
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
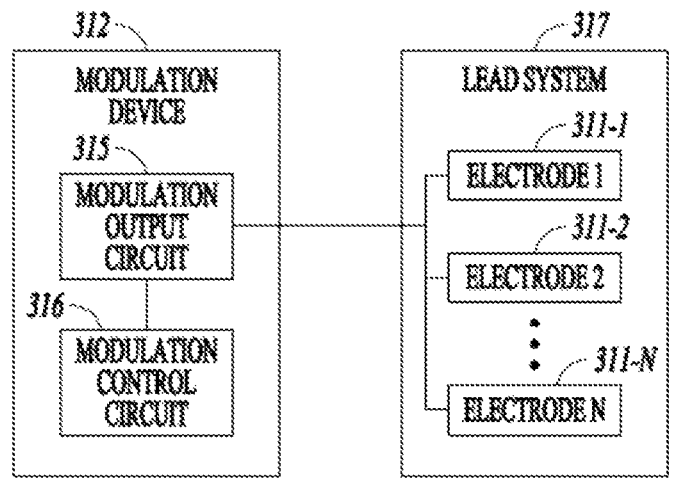
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of available modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets. A closed-loop mechanism may be used to identify and test modulation parameter sets, receive patient or clinician feedback, and further revise the modulation parameter sets to attempt to optimize stimulation paradigms for pain relief. The patient or clinician feedback may be objective and/or subjective metrics reflecting pain, paresthesia coverage, or other aspects of patient satisfaction with the stimulation.

Figure 4:
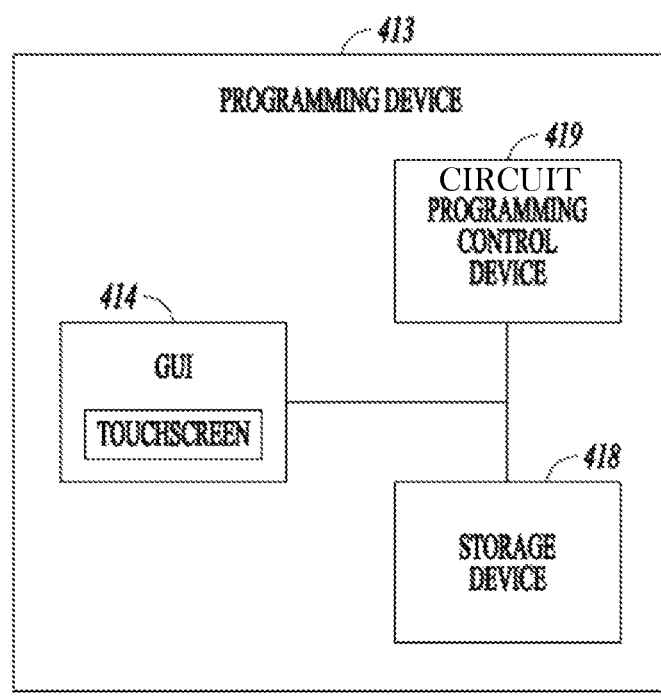
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device (e.g., modulation device 312 of FIG. 3). The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software, and firmware. For example, the circuit of GUI 414, modulation control circuit 316, and programming control circuit 419, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or a portion thereof, and a programmable logic circuit or a portion thereof.

Figure 5:
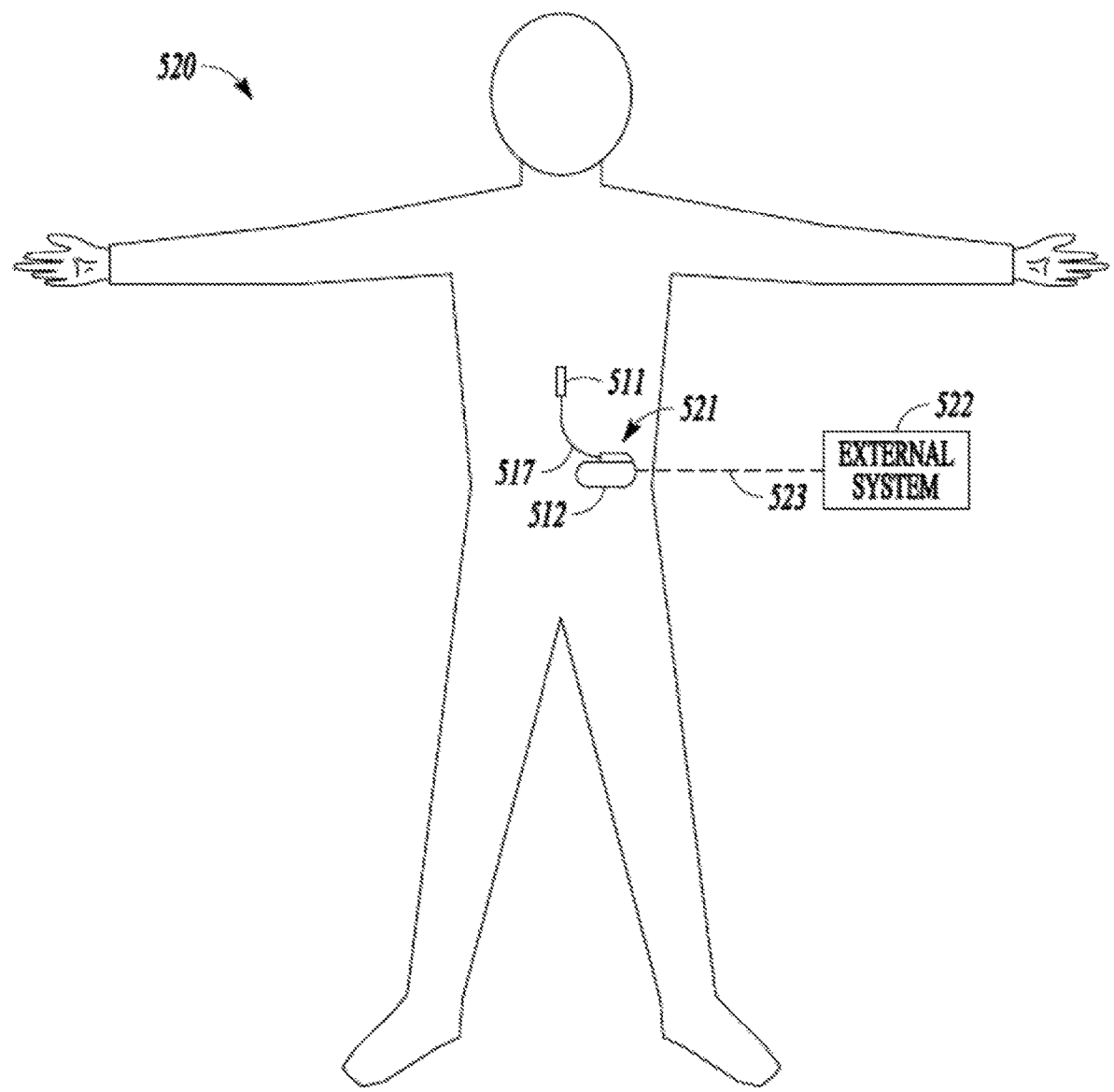
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system 521 is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters. The remote control device may also provide a mechanism for the patient to provide feedback on the operation of the implantable neuromodulation system. Feedback may be metrics reflecting perceived pain, effectiveness of therapies, or other aspects of patient comfort or condition.

The neuromodulation lead(s) of the lead system 517 may be placed adjacent, e.g., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
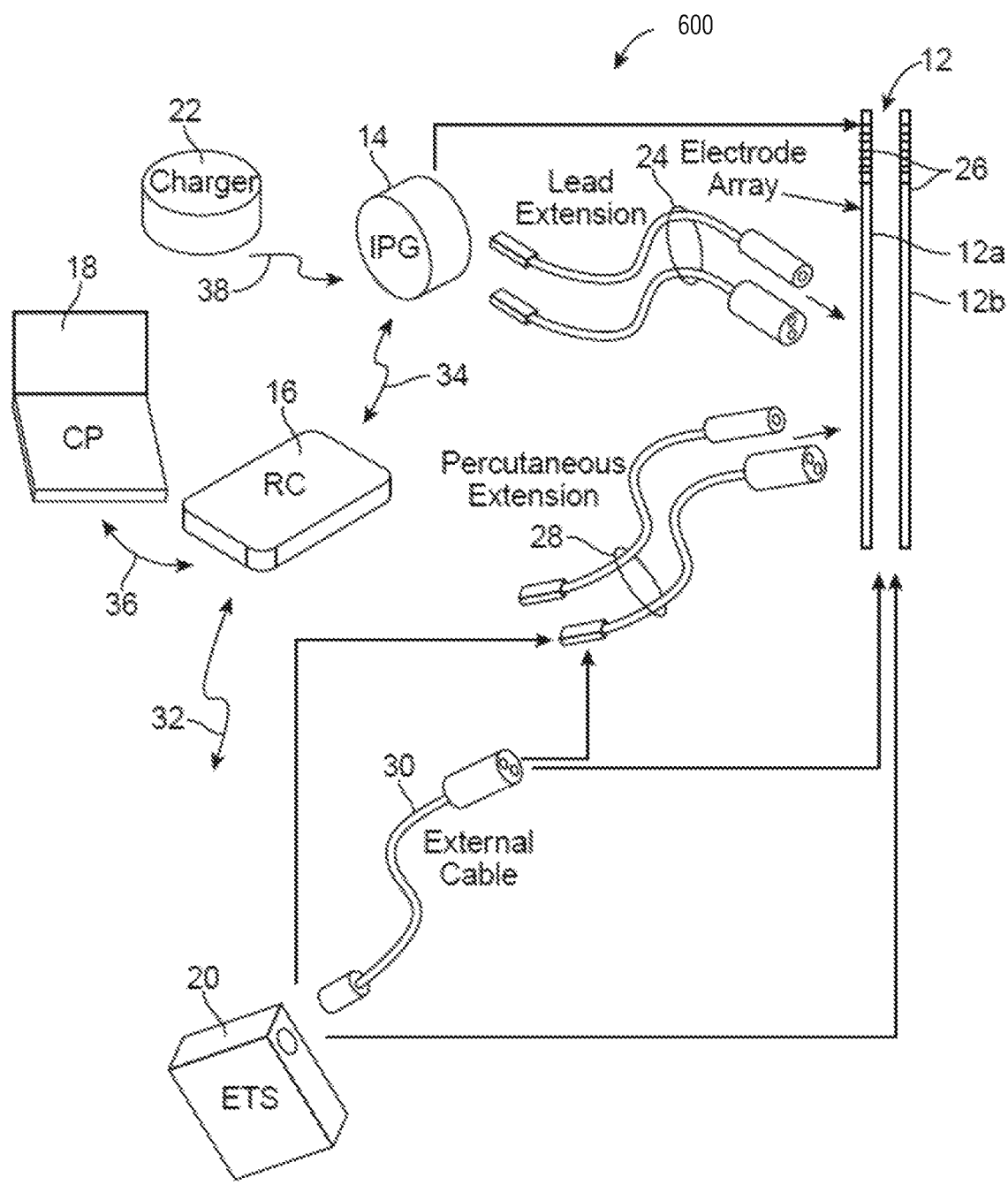
FIG. 6 illustrates, by way of example, an embodiment of an SCS system.

FIG. 6 illustrates, by way of example, an embodiment of an SCS system 600. The SCS system 600 generally comprises a plurality of neurostimulation leads 12 (in this case, two percutaneous leads 12a and 12b), an implantable pulse generator (IPG) 14, an external remote control (RC) 16, a User's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead can be used in place of one or more of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides the user detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. For purposes of brevity, the details of the RC 16, ETS 20, and external charger 22 will not be described herein.

Application of Automated Programming for Sub-Perception Stimulation Parameters

Sub-perception neuromodulation therapy is a promising area that may potentially improve patient outcomes. There are numerous potential sub-perception therapies, so one problem is determining which of the many possible sub-perception therapies may provide the best outcome for the patient. The problem is compounded by the fact that it frequently takes hours or days for a sub-perception therapy to become effective. Without immediate feedback for the health care provider or manufacturer representative it may involve repeat follow-up visits to identify and fine-tune the optimal sub-perception therapy for each individual patient. An adaptive learning algorithm that can identify the optimal sub-perception therapy for a patient without requiring intensive health care provider or manufacturer interaction would have significant clinical and commercial potential.

Software or hardware in the implantable pulse generator (IPG), programming device, or patient remote control may be used during a trial period or after permanent implant to identify the optimal sub-perception modality.

A machine learning system may be used in a closed-loop process to develop optimized stimulation patterns for pain management. The stimulation patterns may be modulated in both the time and space domains. The stimulation patterns may also be modulated in the informational domain, which refers to the patterns of pulses. The learning system may automatically cycle through different sub-perception modalities (e.g., high frequency, burst, low-mid frequency/low amplitude, etc.), collect patient feedback through a remote control or other system on each of the modalities, and correlate patient feedback with therapy efficacy in order to determine an optimal or improved therapy. This allows for improved or optimal sub-perception therapy to be determined without interaction with the health care provider or manufacturer representative.

An initial set of stimulation patterns may be generated from a domain of all available stimulation patterns. The initial set may be obtained using one or more machine learning or optimization algorithms to search for and identify effective patterns. Alternatively, the initial set may be provided by a clinician.

In addition to the initial set of parameter settings, one or more ranges for one or more parameters may be determined by the system or provided by a user (e.g., clinician). The ranges may be for various aspects including amplitude, pulse width, frequency, pulse pattern (e.g., predetermined or parameterized), cycle on/off properties, spatial location of field, spatial extent of field, and the like.

Estimated times for wash-in and wash-out may be provided by a user or determined by the system. In an embodiment, the system estimates the wash-in/out to be used from the patient feedback. Accurate estimates for wash-in/out are important because over-estimates (e.g., too long of a period) may result in patients having unnecessary pain because the programming cycles too slowly, and under-estimates (e.g., too short of a period) may result in missing important information because the wash-in has not occurred. So, in an embodiment, a user is able to set the expected wash-in/out times for the learning machine algorithm to use. In a further embodiment, the learning machine algorithm may then begin with the user estimate and then adjust based on data collected from the user or other sources to revise the estimated wash-in or wash-out times.

In the clinical system, a patient may be provided one or more stimulation patterns, which may be tested by the patient with or without clinician supervision. Objective pain metrics, subjective pain metrics, or both objective and subjective pain metrics may be received from the patient, which are used in the machine learning or optimization algorithms to develop further sets of patterns. Objective pain metrics include those that are physiologically expressed, such as EEG activity, heart rate, heart rate variability, galvanic skin response, or the like. Subjective pain metrics may be provided by the patient and be expressed as "strong pain," "lower pain," or numerically in a range, for example. The pain metrics may be communicated using various communication mechanisms, such as wireless networks, tethered communication, short-range telemetry, or combinations of such mechanisms. The patient may manually input some information (e.g., subjective pain scores).

A non-exhaustive list of pain metrics is provided herein. One example of a pain metric is EEG activity (e.g., Theta activity in the somatosensory cortex and alpha and gamma activity in the prefrontal cortex have been shown to correlate with pain). Another example pain metric is fMRI (activity in the anterior cingulate cortex and insula have been shown to correlate with changes in chronic pain). Another example pain metric is fMRI (activity in the pain matrix, which consists of the thalamus, primary somatosensory cortex, anterior cingulate cortex, prefrontal cortex, and cerebellum and is activated in pain conditions). Another example pain metric is heart rate variability, galvanic skin response, cortisol level, and other measures of autonomic system functioning (autonomic system health has been shown to correlate with pain). Another example pain metric is physical activity (amount of physical activity has been shown to correlate with pain). Another example pain metric is pain scores (may be inputted through an interface where the patient selects a point on a visual analog scale, or clicks a number on a numerical rating scale). Another example pain metric is quantitative sensory testing [e.g., spatial discrimination (two-point, location, diameter), temporal discrimination, detection threshold (mechanical, thermal, electrical), pain threshold (mechanical, thermal, electrical), temporal summation, thermal grill] (QST measures have been shown to correlate with pain). Another example pain metric is somatosensory evoked potentials, contact heat evoked potentials (these have been shown to be correlated with pain). Another example pain metric is H-reflex, nociceptive flexion reflex (these have been shown to be reduced by SCS). Another example pain metric is conditioned place preference (e.g., in one chamber, stimulate with one paradigm 1, in other chamber, stimulate with paradigm 2. The chamber where the animal spends the most time wins and continues to the next round.). Another example pain metric is local field potential recordings in the pain matrix (recordings of neural activity in these areas are possible with invasive electrodes in a preclinical model).

Some pain metrics are primarily preclinical in nature (e.g., conditioned place preference and local field potential recordings), while others are primarily clinical in nature (e.g., pain scores and quantitative sensory testing). However, it is understood that the pain metrics may be obtained in either preclinical or clinical settings.

Pain metrics may be continuously or repeatedly collected from patients and fed into the machine learning or optimization algorithms to refine or alter the stimulation patterns. For example, the patients may interact with a programmer, remote control, bedside monitor, or other patient device to record physical condition, pain, medication dosages, etc. The patient device may be wired or wirelessly connected to the system with the machine learning system. This closed-loop mechanism provides an advantage of reducing the search domain during repeated iterations of the machine learning or optimization algorithm. By reducing the search domain, a clinician is able to more quickly identify efficacious patterns and a patient may be subjected to shorter programming sessions, which produce less discomfort.

In addition to pain metrics, additional patient feedback may be obtained, such as a satisfaction evaluation, self-reported activity, visual analog scale (VAS), or numerical rating scale (NRS). Other feedback and input may be obtained, such as from a user (e.g., clinician) or sensor values.

The physical system may take on many different forms. Data collected from the patient may be measured using wearable sensors (e.g., heart rate monitor, accelerometer, EEG headset, pulse oximeter, GPS/location tracker, etc.). The pain metrics and other feedback involving manual input may be entered via remote control or other external device used by the patient (e.g. cellular phone).

The algorithm may reside on the CP, the IPG, the ETS, the RC or other external device used by the patient, or in the cloud or remote servers connected to patient external via Wi-Fi, Bluetooth, cellular data, or other wired/wireless scheme. There may be a GUI on the CP, remote control, or other external device, that enables selection of algorithm as well as manual input. Training of the algorithm may take place in the clinic or in daily life, and may be set to be execute continually or only at certain times. Optimization data may be stored in the cloud so that optimized patterns and history can be transferred when the patient moves from trial to permanent implant and also if the IPG is replaced.

Figure 7:
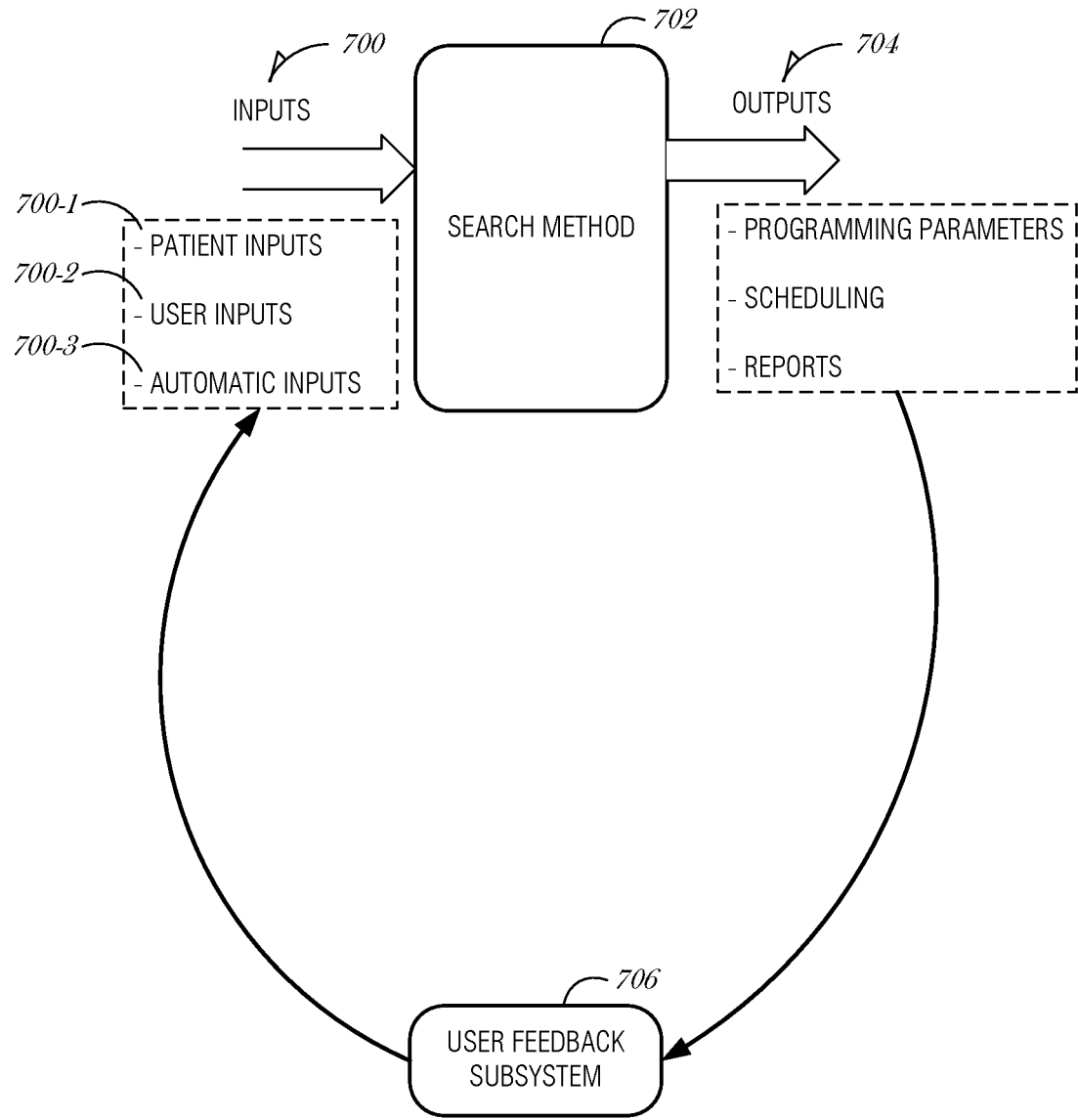
FIG. 7 illustrates, by way of example, an embodiment of data and control flow in a system that utilizes machine learning to optimize neurostimulation patterns.

FIG. 7 illustrates, by way of example, an embodiment of data and control flow in a system that utilizes machine learning to optimize neurostimulation patterns. One or more inputs 700 may be fed into a search method 702, which may then provide one or more outputs 704. The inputs 700 may be generally grouped as patient inputs 700-1, user inputs 700-2, and automatic inputs 700-3. Outputs 704 may include programming parameters or scheduling, reports, and other actions. In addition, a user feedback subsystem 706 may be used to query a user (e.g., a patient) and obtain feedback regarding current, previous, or future programming, pain or quality of life scores, or other information.

Inputs 700 may include patient inputs 700-1. Patient inputs 700-1 may include a wide variety of patient data, such as subjective patient pain scores or quality of life scores in the form of a visual analog scale (VAS) or numerical rating scale (NRS), satisfaction scores, a Global Impression of Change metric, self-reported activity, or some mathematical combination of such metrics (e.g., a weighted sum of VAS and activity).

User inputs 700-2 may include various clinician or specialist inputs, such as programs to evaluate or dimensions to evaluate (e.g., x, y, frequency, pulse width, duty cycle, number of pulses per burst, inter and intra-pulse frequency for burst waveforms, etc.). Other user input 700-2 may include ranges of a parameter to test or threshold values (e.g., minimum or maximum values for a particular parameter (e.g., up to 6.0 mA or from 1.0-5.5 mA). User input 700-2 may also include the amount of time to evaluate a program before moving to another program, a patient option to skip a program (e.g., when the patient feels like the program is not being effective and there is still two days left in the evaluation time period), a minimum evaluation time before skipping (either programmatically or patient-initiated skip), a survival threshold, or search objectives. The survival threshold may be used to determine whether based on patient feedback, a particular parameter set is retained or discarded from future consideration. For example, a clinician may set a survival threshold of 7.0, such that if a patient experiences a VAS score greater than 7.0, then the programming associated with the score is discarded from future evaluation. Additional, the search method 702 may be modified to discard the programming (e.g., in a genetic algorithm, the programming may be removed from the chromosome pool so that it is not used in future generations).

A search objective may be provided by the patient or clinician (or other user). The search objective may tune the search method 702 to work toward a program that achieves a desired outcome. One or more objectives may be selected. When more than one objective is selective, the combination of objectives may be weighted or ranked. Examples of objectives include, but are not limited to a lower charging frequency, more efficient energy usage, maximize pain relief, usage of paresthesia, absence of paresthesia, specified pain relief threshold (e.g., work to achieve a specified VAS score or comfort level), pain relief in one or more specified areas (e.g., lower back, foot, leg, etc.), bias towards specific wave forms or field shapes (e.g., burst waveforms, high rate, long pulse width, etc.), stimulation at specified vertebral levels, or minimum/maximum search time for search to explore various programs before the optimal program is determined (e.g., measured in number of generations in a genetic algorithm).

Other user input 700-2 may be received from the patient via the user feedback subsystem 706. The user feedback subsystem 706 may interface with one or more devices (e.g., the CP, the IPG, the ETS, the RC, or another external device used by the patient or clinician) and obtain patient feedback (subjective or objective), sensor data, clinician feedback, or the like. Patient feedback may be a "best so far" rating of recent programming settings, "worse/same/better" rating than a previous program, patient indications of comfort, activity, or mood. Various objective data may be obtained as well via the user feedback subsystem 706, such as activity, impedance/field potential signature, heart rate, heart rate variability, field potentials, and the like. The objective data may be used to determine an objective measurement of pain, a surrogate measurement of comfort or quality of life (e.g., more or less recorded activity may be associated with less or more discomfort, respectively), or performance data of a particular programming. The user feedback system 706 may also collect and communicate patient user interface actions, such when a patient selectively terminates a programming session, skips a programming session, or a rank of two or more programming sessions provided by the patient. The sorted programs may be used as input to the search method 702 to select, filter, focus, or otherwise modify the search method 702 in future iterations of the patient feedback loop.

Automatic inputs 700-3 may include some or all of the objective data that may be collected via the user feedback subsystem 706 (e.g., activity, heart rate, etc.). For example, an accelerometer may be used to identify, classify, and obtain patient posture, activity, or the like. Other automatic inputs 700-3 may include performance data, such as the duration of a programming session, the number of time a parameter set was tested and the related patient scores/feedback, etc.

Some or all of the outputs 704 may be fed to the user feedback subsystem 706 for presentation to one or more users. For example, a weekly report of the programming used may be provided to a user (e.g., a patient). The output 704 may be used to drive further processing on the user feedback subsystem 706 in order to obtain patient inputs 700-1 or user inputs 700-2, which may be fed back into the search method 702 and used to determine additional outputs 704.

The user feedback subsystem 706 may be hosted at an external device (e.g., a central server or a cloud server) and communicatively coupled to one or more devices, including but not limited to the CP, the IPG, the ETS, or the RC. In addition, or alternatively, the user feedback subsystem 706 may be partially or fully hosted at one of the devices, such as the CP or the RC.

The user feedback subsystem 706 may provide a user interface to a user. The user interface (UI) may include various user interface controls, such as a body diagram to allow the user to indicate where pain is felt on a body, drop down menus, dialog boxes, check boxes, or other UI controls to allow the user to input, modify, record, or otherwise manage data representing a patient's comfort level, activity level, mood, or other general preferences to control the search method 702 or a stimulator's operation. The UI may prompt the user for various information, such as a daily survey of whether the current programming is worse, same, or better than a previous programming. The UI may also provide a user with an interface to sort a number of programs according to the patient's preference. An example UI is illustrated in FIGS. 8A and 8B.

Figure 8A:
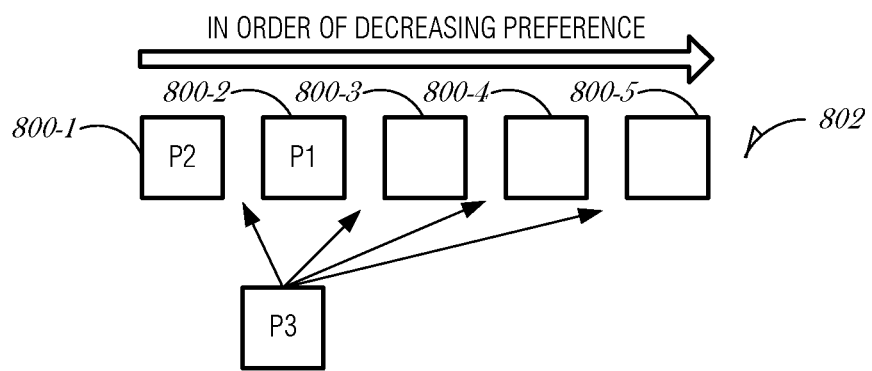
FIGS. 8A-8B illustrate, by way of example, another embodiment of data and control flow in a system that utilizes machine learning to optimize neurostimulation patterns.
Figure 8B:
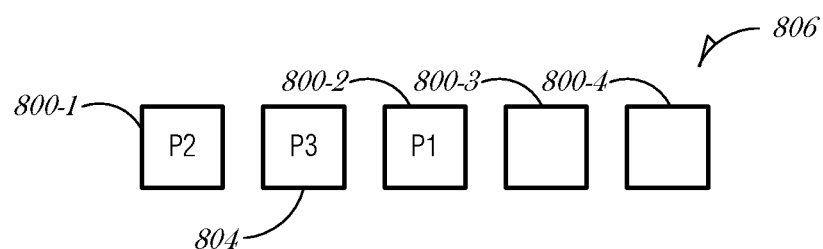

FIGS. 8A and 8B illustrate, by way of example, an embodiment of a user interface to sort programming. In FIG. 8A, the initial state, a number of user interface elements 800-1, 800-2, 800-3, 800-4, 800-5 are represented in an ordered fashion. The number of user interface elements in FIG. 8A is five, but it is understood that other numbers of user interface elements may be used, such as, but not limited to ten, twenty, or fifty. In the first instance 802, the UI elements 800 include P1 and P2, which correspond to the first and second programming sets that the patient experienced. The patient is provided user interface element 804, which represents the third programming set P3, to insert among the ordered UI elements 800. The patient may move the UI element 804 to place it in order of perceived performance (e.g., preference). In this example, the patient opts to place UI element 804 in between UI elements 800-1 and 800-2, indicating that the programming P3 was better than P2, but worse than P1. In FIG. 8B, the subsequent state 806, after dragging and dropping the UI element 804 to the selected position, the other UI elements 800 are rearranged around the newly inserted UI element 804. If a programming set was in the last position (e.g., 800-5), then it is bumped from the list and the programming set in the fourth position (e.g., 800-4) is demoted to the last position. In addition, the user may adjust the order of the programming sets by dragging and dropping one UI element from one position to another, in which case, the other UI elements are rearranged in the new order.

Returning to FIG. 7, additional user interface controls may be provided to a user (e.g., a clinician or a patient) to set test periods for a program, manage wash-in/out time, provide user reports with raw data or compiled data (e.g., charts, graphs, summaries), or control alternating programs. For example, a "best so far" (BSF) program may be used and reused over time to ensure that the patient experiences a good percentage of effective stimulation. The BSF program may be used as every other program, every third program, or in other ways to allow the system to test additional programs in between the BSF program.

In an embodiment, the user interface for the patient may obscure some or all of the programming details, in effect blinding the patient from the program being used. This may be an option and may be settable by the clinician (e.g., via the CP such that the RC does not display certain information). By doing so, the patient may not be biased based on certain settings or values.

A number of different mechanisms may be used in the search method 702. Examples include, but are not limited to a sorting algorithm, a gradient descent method, a simplex process, a genetic algorithm, a binary search, and sensitivity analysis. Any of the methods may include a pruning process, where programs that do not perform within some satisfactory range are removed from future use or consideration in a search. For example, a program that uses high frequency and causes major discomfort in a patient may be removed from use in future mutations or crossovers in a genetic algorithm search.

Figure 9:
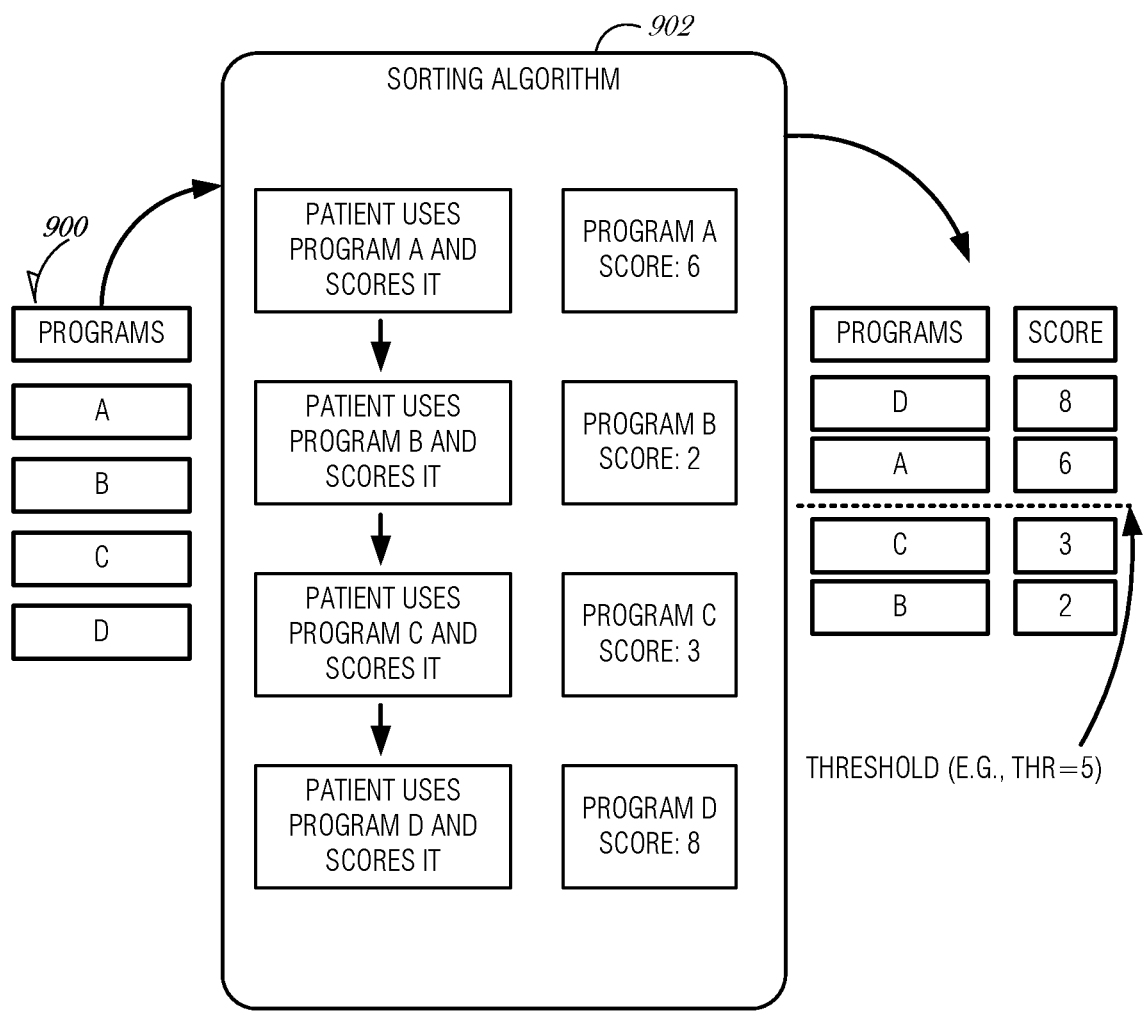
FIG. 9 illustrates, by way of example, an embodiment of constructing stimulation waveforms in space and time domains.

FIG. 9 illustrates, by way of example, an embodiment of a sorting algorithm used as a search method. In general, the sorting algorithm provides a series of programs, receives user feedback on each program's efficacy, and sorts the programs according to the user's feedback. In the example embodiment illustrated in FIG. 9, a patient is scheduled for four programs 900. The patient may be put on a program, e.g., Program A, for a period of time. The period may vary or may be fixed. The period may be calculated to ensure that the patient is on the program for a sufficient amount of time for wash-in/out before the patient is to evaluate the program. The patient may provide a score. In the example illustrated in FIG. 9, the score is based on a combination of activity and NRS. Activity may be rated on a numerical scale, such as the number of hours a patient was active in a given day or an average number of hours that the patient was active in a given week. Other metrics of activity are considered to be within the scope of this disclosure.

Using the activity metric and the NRS, a score is derived and provided to the sorting algorithm 902 (e.g., search method). The sorting algorithm 902 may then transition to the next program from the scheduled programs 900. The parameters for the next program (e.g., Program B) are communicated to the patient device (e.g., IPG) and used for a period of time.

After the evaluation period, the patient scores the program and the result is communicated back to the sorting algorithm 902 (e.g., from the user feedback subsystem 706). This evaluation loop may continue through the scheduled programs 900 and on to other programs. The sorting algorithm 902 may maintain a sorted data structure of scores 904, where programs are sorted based on the score provided by the patient. A predefined threshold may be used to discard any programs that fail to meet a minimum score. In the example illustrated in FIG. 9, the threshold is five. As such, Program C and Program B are discarded and Programs D and A are kept for additional evaluation. For example, Programs D and A may be used together or individually in a subsequent schedule of four programs so that the patient can evaluate them against other programs. In this example, a higher score reflects a better program. This is fine for composite scores, but for NRS, which usually uses lower scores as better (meaning less pain), the comparisons and thresholds may be adapted accordingly.

Figure 10:
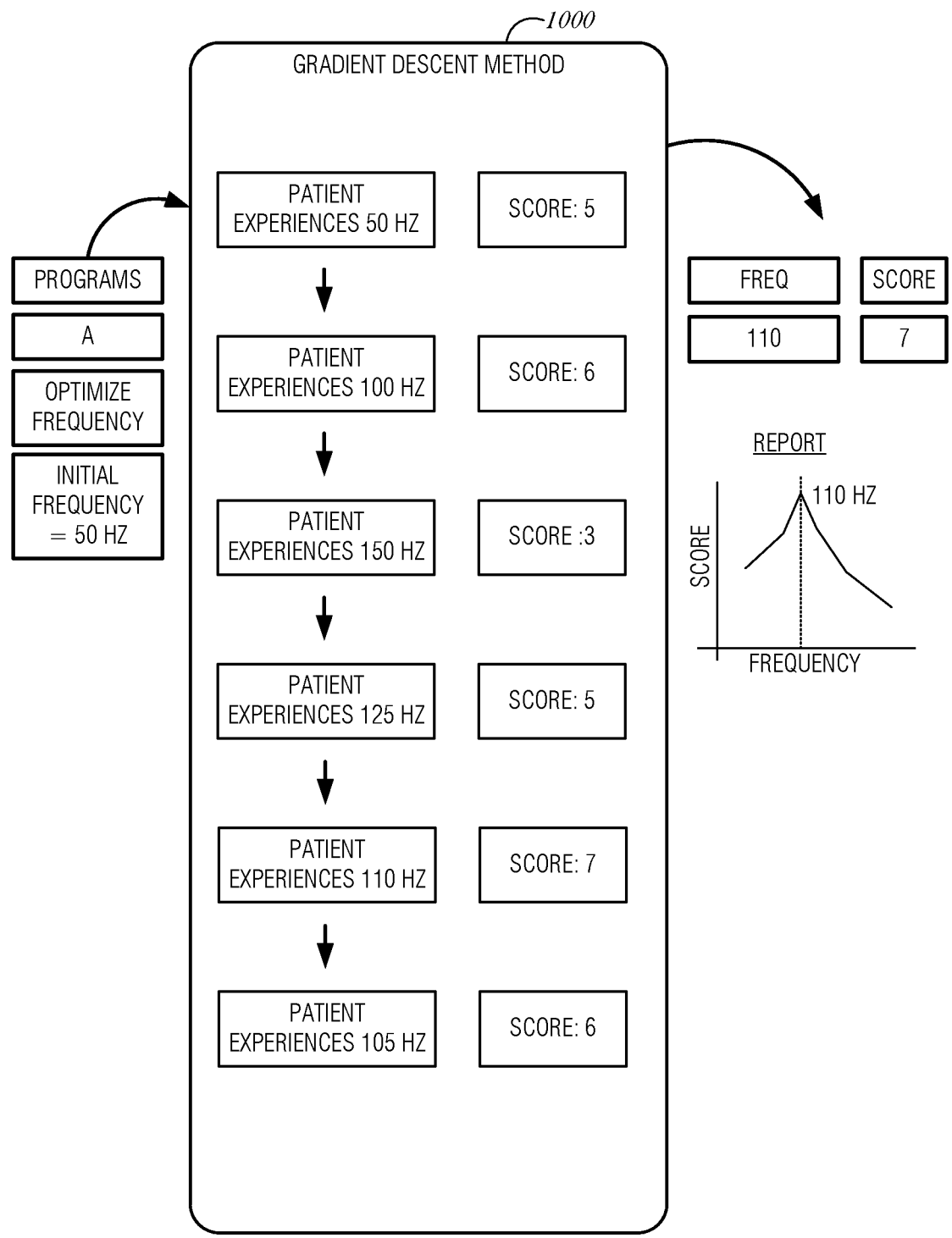
FIG. 10 illustrates, by way of example, an embodiment of a system that utilizes machine learning to optimize neurostimulation patterns.

Another search method 702 is illustrated in FIG. 10, which illustrates, by way of example, an embodiment of a gradient descent method used as a search method. In general, the gradient descent method is given an aspect of programming to optimize and an initial value for the aspect. The gradient descent method then searches for the local optimal value for the aspect. If the method is used to find a local maximum of the function, the procedure is then known as a gradient ascent method. For the purposes of this discussion, the term gradient descent will be used, but it is understood that when seeking a local maximum, the term gradient ascent may also be applicable.

Figure 16:
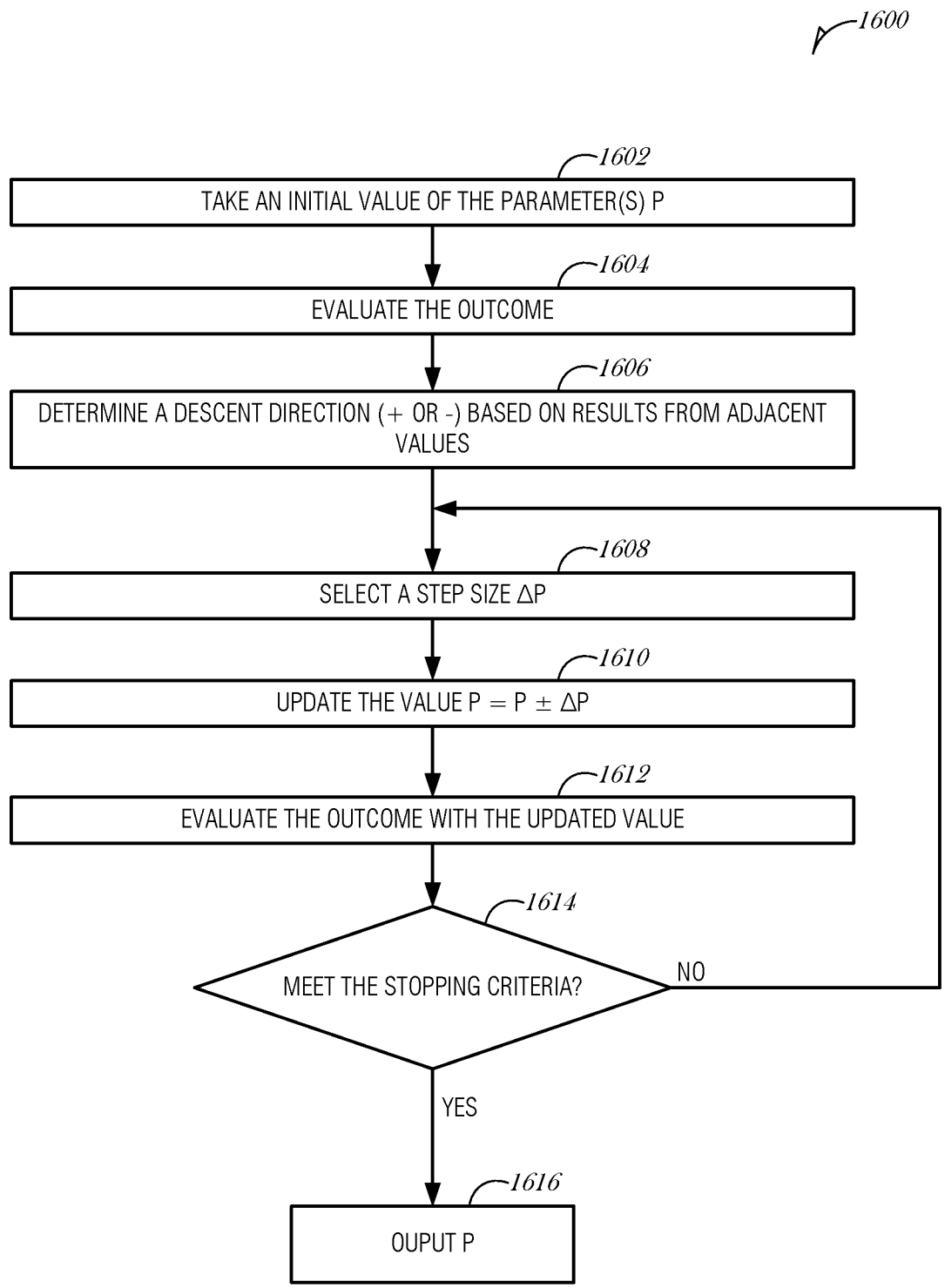
FIG. 16 illustrates, by way of example, an embodiment of a gradient descent method.

FIG. 16 illustrates, by way of example, an embodiment of a gradient descent method 1600. At block 1602, an initial value of the parameter(s) P is taken. The outcome of the parameter(s) P is evaluated (block 1604). This establishes a starting point for the rest of the evaluations. At block 1606, a descent direct (+ or −) is determined based on the results from adjacent values of P. For example, a value higher than the initial value of P is evaluated and a value lower than the initial value of P is evaluated. Based on which value shows a better result, the descent method 1600 is set to an increasing direction or a decreasing direction. At block 1608, a step size ΔP is selected. The ΔP may be a value based on the initial value of P. For example, if the initial value of P is 200, the ΔP step size may be 50% of the current value of P, such that the ΔP=100. At block 1610, the value of P is updated by the ΔP in the direction determined at operation block 1606. At block 1612, the outcome is evaluated using the new value of P. At block 1614, it is determined whether the method 1600 has met a stopping criteria (e.g., outcome reaches a local minimum). If the stopping criteria is met, then the method 1600 ends at block 1616 and the value P is output. Otherwise, the method 1600 iterates to block 1608 to continue processing.

As an example, in FIG. 10, the gradient descent method 1000 is provided a program 1002 with an indication to optimize on frequency, beginning with an initial frequency value of 50 Hz. The gradient descent method 1000 begins with the initial values and the patient's device is programmed with the initial values (e.g., 50 Hz frequency). The patient may be progressed through a number of programs that are guided by the gradient descent method 1000.

In the example illustrated in FIG. 10, the gradient descent method 1000 begins with a 50 Hz frequency, relates it to a score obtained from the patient via patient feedback, and then progresses to the next program, which may use a step value of the initial value. Other step values may be used, such as a fixed number (e.g., increase/decrease by 10 Hz), percentage (e.g., increase/decrease by 100% of the initial value), or other mechanisms. As illustrated, the step value is used until a score is received that indicates a decreased program performance. In particular, the patient is first presented with a program using 50 Hz frequency, which is scored a five. Then the patient is presented with a program using a 100 Hz frequency, which is scored at a higher score of six. Then, using the same step value of 50 Hz, the patient is presented with a program using a 150 Hz frequency, which is scored a lower score of three. At this point, the gradient descent method 1000 seeks to find the local optimal value between the two values of 100 Hz and 150 Hz. Continuing with the example, the gradient descent method 1000 tests 125 Hz and finds that it is better than 150 Hz, so it continues reducing the Hz value to seek the next point of deflection (where the scoring trend changes). The gradient descent method 1000 reduces the Hz to 110 Hz and receives a score of seven, which is an increase over the score at 125 Hz. The gradient descent method 1000 then tests a value between 100 Hz and 110 Hz (e.g., 105 Hz) and may continue in this manner.

The gradient descent method 1000 may maintain the optimal frequency based on the best observed score. In this case, it is a frequency of 110 Hz with a score of seven. The data used in gradient descent method 1000 may also be represented in various reports, such as a line graph, bar chart, or the like to visualize the scoring trends versus the metrics being optimized.

Another search method 702 is sensitivity analysis. Sensitivity analysis can be used to find regions in a space of input factor for which a model output is either maximum or minimum or meets some optimum criteria. In an embodiment, a number N of sets of data may be collected that represent stimulation parameters and corresponding outcomes. The stimulation parameters may include location, amplitude, pulse width, frequency, duty cycle, pattern, fractionalization, etc. Outcome variables may include visual analog scale (VAS), numerical rating scale (NRS), satisfaction, comfort level, global impression of change, activity, or derived outcome measure, etc. Using the stimulation parameters (X) and the outcome variables (Y), a parameter-outcome model may be built. In an embodiment, the parameter-outcome model is a regression model where $Y=f(X, a)$, where a is a vector of k unknown coefficients to be identified. In general, it is better to have $N \geq k$. Using the N sets of data, the sensitivity analysis is applied to assess the significance of the input variables to the output variables. The result of the sensitivity analysis is to identify sensitive parameter sets and insensitive parameter sets.

It is understood that other methods may be used to determine or classify sensitive/insensitive parameter sets, such as machine learning, neural networks, or guided selection. With guided selection, a user may be presented with various stimulation parameter sets and may drop the insensitive parameters, focusing on the sensitive parameter adjustment. Users may have the option to include insensitive parameters during later stimulation testing. Using sensitivity analysis, a system may automatically choose dimensions or recommend default stimulation parameters.

It is understood that in various embodiments, given $Y=f(X, a)$, a may be a matrix or a vector depending on the dimension of X and Y, e.g., X is k×N, and Y is m×N, that is, for each set of X of k stimulation parameters, there is a set of outcome evaluations Y of m outcome variables. The a would be a coefficient matrix of m×k that represents the significance of each of the stimulation parameters to each of the outcome variables.

Figure 15:
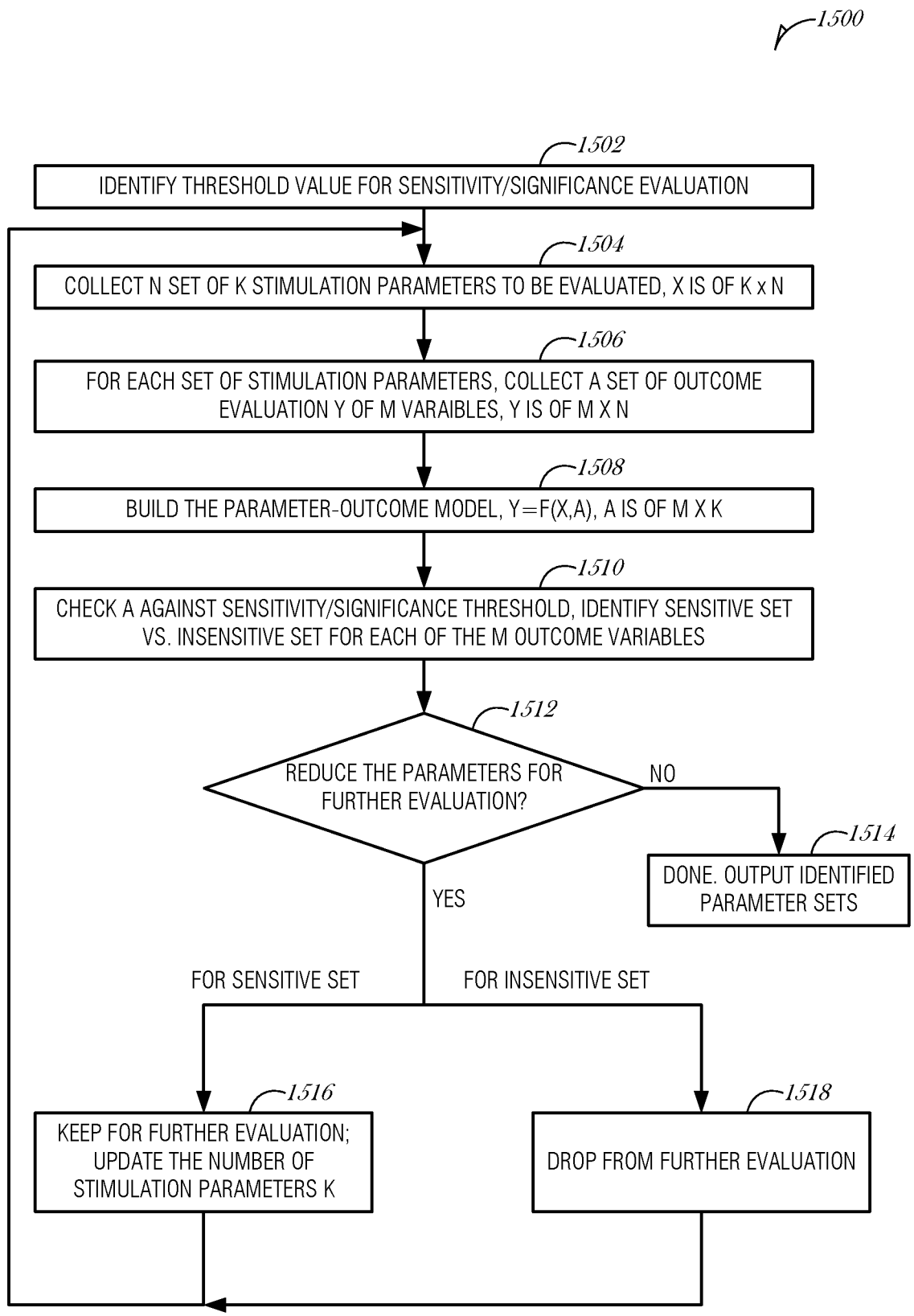
FIG. 15 illustrates, by way of example, an embodiment of a method that identifies parameter sets.

FIG. 15 illustrates, by way of example, an embodiment of a method 1500 that identifies parameter sets. At block 1502, a threshold value for sensitivity/significance evaluation is identified. At block 1504, a set N of k stimulation parameters to be evaluated is collected, wherein X is of k×N. At block 1506, for each of the stimulation parameters, a set of outcome evaluation Y of m variables is collected, where Y is of m×N. At block 1508, the parameter-outcome model $Y=f(X, a)$ is built, where a is of m×k. At block 1510, the value a is checked against the sensitivity/significance threshold to identify sensitive sets versus insensitive sets of each of the m outcome variables. At block 1512, it is determined whether to reduce the parameters for further evaluation. If the outcome of the determination at block 1512 is negative, then at block 1514, the method 1500 is complete and the parameter sets are output (both the sensitive set of parameters and the insensitive set of parameters). The method 1500 may output both subsets (sensitive set and insensitive set), so that further processing or actions may be taken on them, for example, the sensitive set may be used to guide the programming of therapeutic stimulation and insensitive set may be used to guide the creation of variation in stimulation parameters if needed (e.g. to prevent adaptation to fixed stimulation parameters) but does not significantly alter the therapeutic effect. If the outcome of the determination at block 1512 is affirmative, then for a sensitive set, at block 1516, the set is kept for further evaluation and the number of stimulation parameters k is updated. For an insensitive set, at block 1518, the insensitive set is dropped from further evaluation, but recorded for later use (as previously described). The method 1500 continues to block 1504 for continued execution. Continued iterations of the method 1500 refine the sensitive subset to provide additional levels of sensitivity analysis.

It is understood that the user may bound the search space in any of the search methods discussed in this document. The user may bound one or more of location bounds, location discreet points, pulse width bounds, frequency bounds, or amplitude bounds.

In addition, it is understood that the search methods may be used to determine time or space parameters for stimulation. A brief discussion of time and space parameters is provided herein.

For the purposes of this discussion, a stimulation protocol may be considered as a construction of building blocks beginning with a pulse. A pulse is single waveform and typically has a timescale in the millisecond range. A burst is a sequence of pulses and may have a timescale on the millisecond to second range. A train is a sequence of bursts and may have a timescale of millisecond, seconds, or even minutes depending on the programming used. A programming sequence is a combination of pulses, bursts, and trains. The programming sequence may also include pauses; periods with no electrical stimulation. A programming sequence may be cyclical over short durations or be non-cyclical over a short duration, but repeat over some longer "macropulse" duration.

In a pulse burst or a pulse train, the intervals between pulses may be regular or irregular. In general, the time domain includes stimulation parameters that control the timing, size, or shape of pulses. Time domain parameters include, but are not limited to, the pulse rate, pulse amplitude, pulse shape, pulse width, and interpulse delay (e.g., between bursts or trains).

In addition to the characteristics of the pulses, the location and direction of stimulation may be controlled using stimulation parameters in the space domain. Various spatial domain parameters include, but are not limited to, lead activation (e.g., which lead(s) are active/inactive), electrode activation (e.g., which electrode(s) in a lead are active/inactive) and active contact fractionalization (e.g., of the active electrodes, how much current is supplied to each active electrode in a lead).

Figure 11:
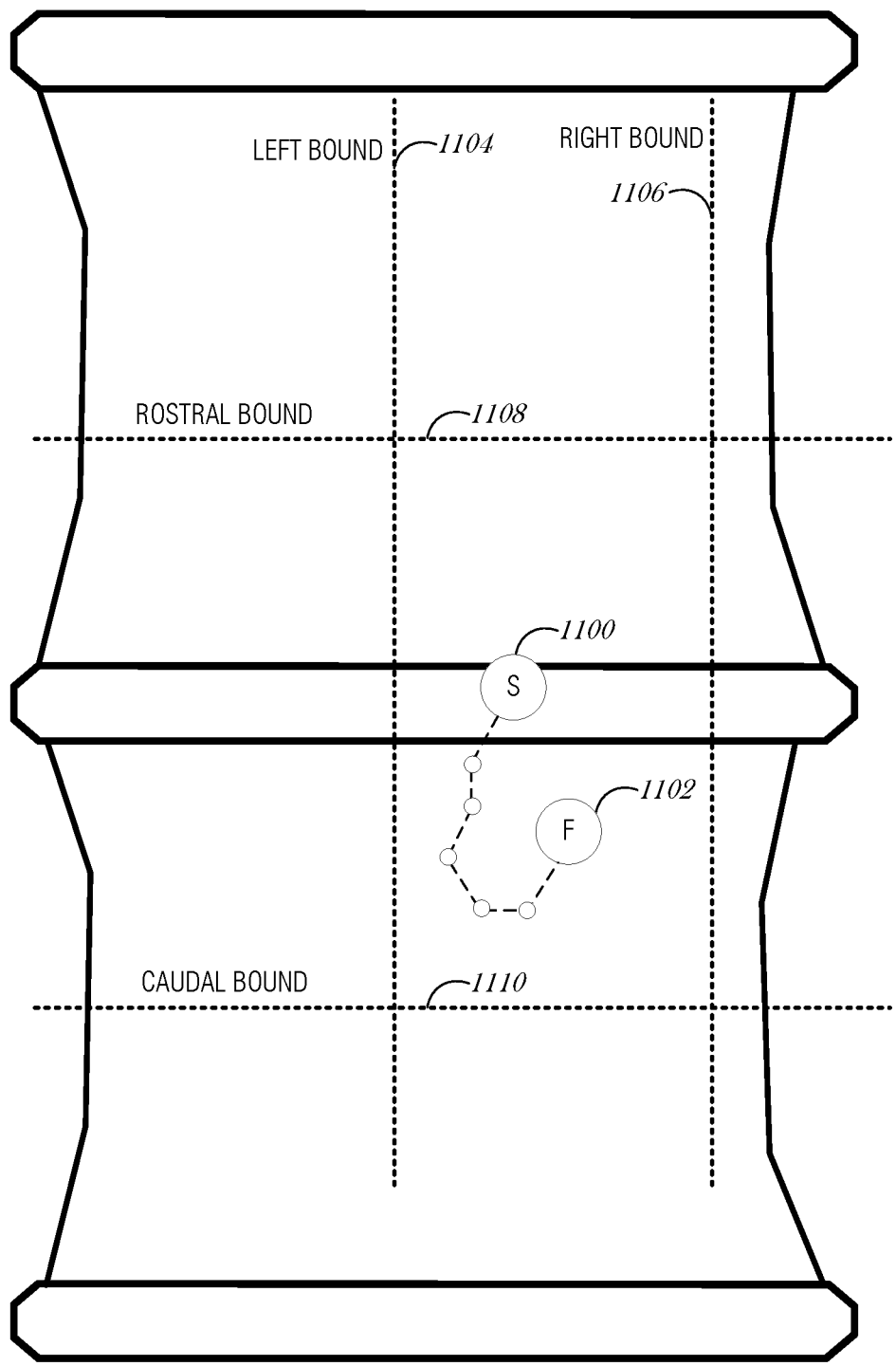
FIG. 11 illustrates, by way of example, an embodiment of a method that utilizes machine learning to optimize neurostimulation patterns.

The search method 702 may search for a best location among a set of possible locations to apply stimulation (e.g., spatial domain parameter). As illustrated in FIG. 11, the search method 702 may be provided with a starting location S 1100 and then use an optimization approach to determine a final location F 1102. Beginning at the starting location 1100, the search method 702 may progress through one or more test points until it finds an optimal point, which is then considered the final location 1102. The test points may be defined as a target volume of activation (VOA), target field, or target pole, in various embodiments. Test points may be defined by contact locations. Test points may be provided by a user (e.g., user selected test points). Alternatively, the test point target pole may be a virtual or ideal pole or multipole pole (e.g., a virtual bipole or tripole). A virtual multipole may be defined by computing field potential values that the virtual multipole creates on an array of spatial observation points, and determining the stimulation amplitude distribution on the electrodes that would result in estimated electrical field potential values at the spatial observation points that best matches the desired field potential values at the spatial observation points. It can be appreciated that current steering can be implemented by moving the virtual multipoles about the leads, such that the appropriate stimulation amplitude distribution for the electrodes is computed for each of the various positions of the virtual multipole. As a result, the current steering can be implemented using an arbitrary number and arrangement of electrodes.

The search method 702 then searches a space for the best point among a set of possible points. The search space may be bounded. In the example illustrated in FIG. 11, the search space is bounded by a left bound 1104, a right bound 1106, a rostral bound 1108, and a caudal bound 1110. Bounds may be clinician/user defined or based on a pain drawing (e.g., using a mapping of probability between pain and ideal stimulation locus). Alternatively, the search method 702 may define bounds during the optimization process (e.g., by using insensitive parameters or pain score thresholding, etc.).

As described above, the search method 702 may program the patient's device (e.g., IPG) with parameters and allow the program to operate for a sufficient time to allow for wash-in/out. Once the patient has some experience with the program, the patient may provide feedback, which is used as input into the search method 702 and may alter the selection or identification of other programs. It is understood that any of the search or optimization algorithms discussed in this document may be used to search for optimal spatial parameters. Additionally, the spatial parameters may be searched in combination with time domain parameters.

The search method 702 may use user feedback. It is understood that a user's comfort level may vary day-to-day or hour-to-hour with the same program. The user's posture, activity level, medication, and other variables may introduce noise into the scores provided by the user. In order to manage the noise in these metrics, one or more techniques may be used. In an embodiment, an overall satisfaction score is used.

As another example, a numerous amount of samples may be taken. Thus, in an embodiment, multiple scores are obtained for a given program. The scores may be averaged, added, or otherwise mathematically combined to obtain an output score.

As another example, objective measures may be obtained and used for corroboration with the patient feedback, used in combination with the patient feedback (e.g., mathematically combined), or used in place of patient feedback. Objective measures may include physiological metrics such as posture, activity, heart rate, heart rate variability, etc.

As another example, repeated evaluations of the same program may be used to recheck and verify a patient's reaction to a given program. Knowingly or unknowingly, the patient may be presented with the same program at a later time and the patient's feedback from the program may be averaged or otherwise combined with previous feedback from an earlier instance of the program's use.

After identifying a good program (or multiple good programs), the IPG may be configured to operate with the identified program(s) for a time until the next re-optimization and reconfiguration. Ideally during this time, the patient has the best program available at that time. However, the patient may experience some neurological conditioning where the patient's neurological system becomes accustomed to the program in a way that the program loses some of its effect on the patient. The result may be the patient experiences more pain or different pain as the days or weeks go by. In an effort to avoid this neurological conditioning, the patient may be provided with a rotating or shifting program schedule. This altering program schedule may provide for neuroplasticity in the patient's neurological system; keeping the patient's neurological system confused and improving the performance or longevity of a program's efficacy. Such programming reduces the need to reprogram, thereby reducing power consumption in the devices in the neuromodulation system and increasing patient quality of life.

Thus, in an embodiment, two or more programs may be cycled on the IPG. The programs may be altered on a regular basis (e.g., changing every seven days) or on an irregular basis (e.g., changing randomly within a five to seven day range). When more than two programs are cycled, the order of the programs may be regular (e.g., cycling in sequence) or irregular (e.g., cycling arbitrarily).

In an example, a burst waveform may run for a specified period before the system automatically shifts to a high rate wave form, with cycling between programs. To avoid a period where pain relief and/or therapeutic effect from the first waveforms (A) ends before the therapeutic effect of the next waveform (B) begins, waveform B may be initiated prior to the termination of waveform A.

Figure 12:
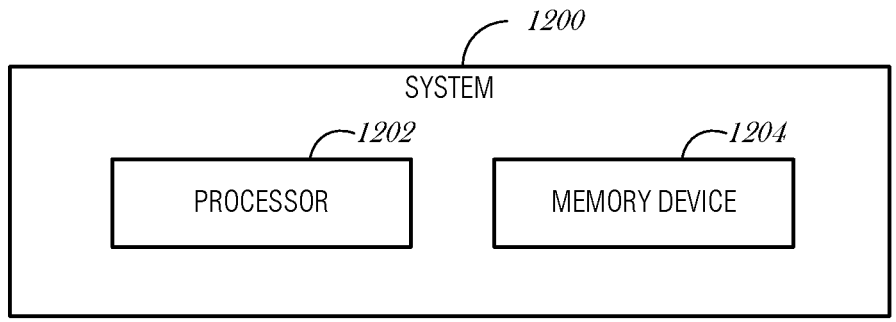
FIG. 12 illustrates, by way of example, an embodiment of a system that utilizes a search method to search for an optimal neuromodulation parameter set.

FIG. 12 illustrates, by way of example, an embodiment of a system 1200 that utilizes a search method to search for an optimal neuromodulation parameter set. The system 1200 may take on one of many forms. The system 1200 may be a remote control or other external device used by a patient or clinician. Alternatively, the system 1200 may be a server or cloud-based device, a network appliance, or other networked device connected via a network (or combination of networks) to a user device. The networks may include local, short-range, or long-range networks, such as Bluetooth, cellular, Wi-Fi, or other wired or wireless networks.

The system 1200 includes a processor 1202 and a memory 1204. The processor 1202 may be any single processor or group of processors that act cooperatively. The memory 1204 may be any type of memory, including volatile or non-volatile memory. The memory 1204 may include instructions, which when executed by the processor 1202, cause the processor 1202 to access at least one of: patient input, clinician input, or automatic input.

In an embodiment, the patient input comprises subjective data. In various embodiments, the subjective data may include comprises a visual analog scale (VAS), numerical rating scale (NRS), a satisfaction score, a global impression of change, or an activity level.

In an embodiment, the clinician input includes a selected neuromodulation parameter set, a selected neuromodulation parameter set dimension, or a search method configuration option. As described elsewhere in this document, the clinician or other user may select one or more programs (e.g., parameter sets) to evaluate. Alternatively or in addition to selecting a program or programs, the clinician or user may select a particular dimension of a parameter set. Dimensions include aspects like frequency or amplitude of a stimulation waveform. Thus, in various embodiments, the selected neuromodulation parameter set dimension comprises a spatial location, a frequency, a pulse width, a number of pulses within a burst or train of pulses, the train-to-train interval, the burst frequency of these trains, a pulse duty cycle, or a burst duty cycle. In addition to programs or dimensions, a user may configure the search method, such as by configuring what the patient can do to modify programs or skip programs, or other aspects of the search methodology. Thus, in various embodiments, the search method configuration option comprises a test range for a neuromodulation parameter set dimension, a termination criteria for a neuromodulation parameter set test, an amount of time to test a neuromodulation parameter set, a minimum evaluation time for a candidate neuromodulation parameter set, or a survival threshold for a neuromodulation parameter set under test.

In an embodiment, the automatic input comprises data received from a patient device. Patient devices include various devices, such as a personal computer (PC), a tablet PC, a hybrid tablet, a personal digital assistant (PDA), a mobile telephone, an implantable pulse generator (IPG), an external remote control (RC), a User's Programmer (CP), an External Trial Stimulator (ETS), or any machine capable of executing instructions (sequential or otherwise) that specify actions to be taken by that machine. In an embodiment, the patient device comprises an accelerometer and the automatic input comprises activity data. In an embodiment, the patient device comprises a heart rate monitor and the automatic input comprises heart rate or heart rate variability. In an embodiment, the patient device comprises an implantable pulse generator and the automatic input comprises field potentials.

The processor 1202 may further use the patient input, clinician input, or automatic input in a search method, the search method designed to evaluate a plurality of candidate neuromodulation parameter sets to identify an optimal neuromodulation parameter set. As described elsewhere in this document, various search methods may be used to evaluate a group of programs or progress through programs to identify an optimal program.

In an embodiment, the search method comprises a sorting algorithm that uses scoring from the patient to sort the plurality of candidate parameter sets and remove parameter sets from the plurality of candidate parameter sets that fail to meet a threshold score.

In an embodiment, wherein the search method comprises a gradient descent system that progresses through the plurality of candidate parameter sets to optimize a dimension of the candidate parameter sets.

In an embodiment, the search method comprises a sensitivity analysis that builds a model from stimulation variables and outcome variables, and uses a regression model to identify a vector of coefficients.

The processor 1202 may further program a neuromodulator using the optimal neuromodulation parameter set to stimulate a patient.

Figure 13:
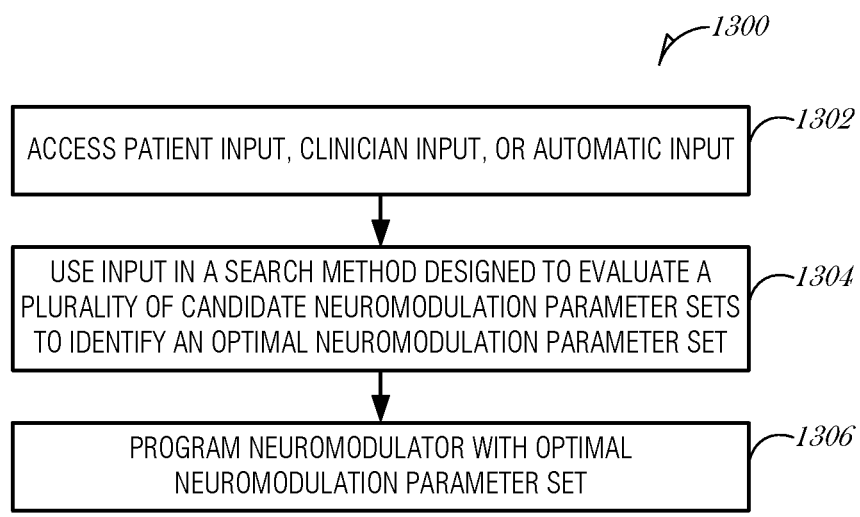
FIG. 13 illustrates, by way of example, an embodiment of a method that utilizes a search method to search for an optimal neuromodulation parameter set.

FIG. 13 illustrates, by way of example, an embodiment of a method 1300 that utilizes a search method to search for an optimal neuromodulation parameter set. At 1302, at least one of: patient input, clinician input, or automatic input is accessed at a computerized system.

In an embodiment, the patient input comprises subjective data. In various embodiments, the subjective data comprises a visual analog scale (VAS), numerical rating scale (NRS), a satisfaction score, a global impression of change, or an activity level.

In various embodiments, the clinician input comprises a selected neuromodulation parameter set, a selected neuromodulation parameter set dimension, or a search method configuration option. In a further various embodiments, the selected neuromodulation parameter set dimension comprises a spatial location, a frequency, a pulse width, a number of pulses within a burst or train of pulses, the train-to-train interval, the burst frequency of these trains, a pulse duty cycle, or a burst duty cycle. In another embodiment, the search method configuration option comprises a test range for a neuromodulation parameter set dimension, a termination criteria for a neuromodulation parameter set test, an amount of time to test a neuromodulation parameter set, a minimum evaluation time for a candidate neuromodulation parameter set, or a survival threshold for a neuromodulation parameter set under test.

In an embodiment, the automatic input comprises data received from a patient device. In a further embodiment, the patient device comprises an accelerometer and the automatic input comprises activity data. In another embodiment, the patient device comprises a heart rate monitor and the automatic input comprises heart rate or heart rate variability. In another embodiment, the patient device comprises an implantable pulse generator and the automatic input comprises field potentials.

At 1304, the patient input, clinician input, or automatic input is used in a search method, the search method designed to evaluate a plurality of candidate neuromodulation parameter sets to identify an optimal neuromodulation parameter set. In an embodiment, the search method comprises a sorting algorithm that uses scoring from the patient to sort the plurality of candidate parameter sets and remove parameter sets from the plurality of candidate parameter sets that fail to meet a threshold score. In an embodiment, the search method comprises a gradient descent method that progresses through the plurality of candidate parameter sets to optimize a dimension of the candidate parameter sets. In an embodiment, the search method comprises a sensitivity analysis that builds a model from stimulation variables and outcome variables, and uses a regression model to identify a vector of coefficients.

At 1306, a neuromodulator is programmed using the optimal neuromodulation parameter set to stimulate a patient.

Figure 14:
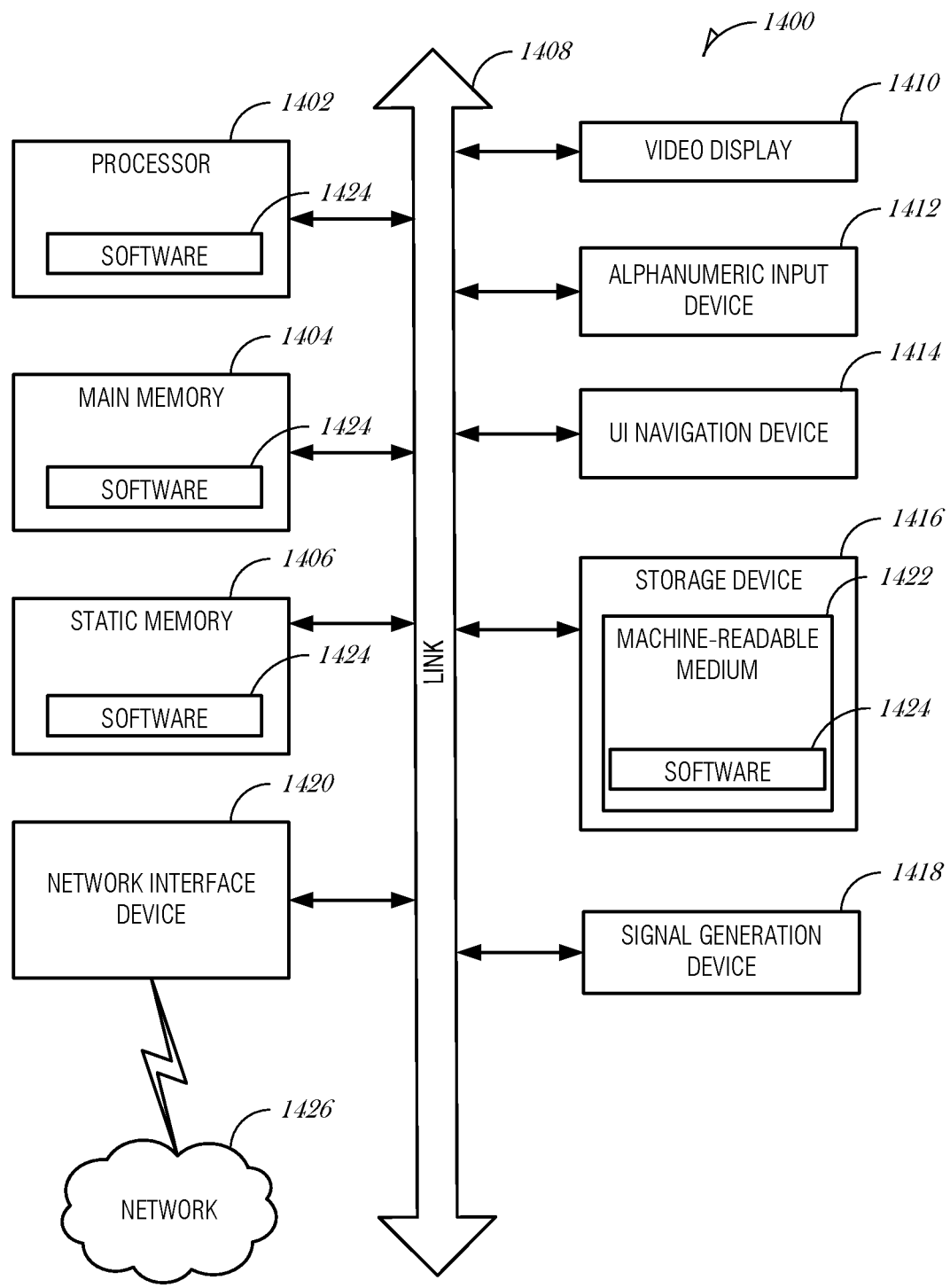
FIG. 14 is a block diagram illustrating a machine in the example form of a computer system, within which a set or sequence of instructions may be executed to cause the machine to perform any one of the methodologies discussed herein, according to an example embodiment.

FIG. 14 is a block diagram illustrating a machine in the example form of a computer system 1400, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may a personal computer (PC), a tablet PC, a hybrid tablet, a personal digital assistant (PDA), a mobile telephone, an implantable pulse generator (IPG), an external remote control (RC), a User's Programmer (CP), an External Trial Stimulator (ETS), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1400 includes at least one processor 1402 (e.g., a central processing unit (CPU), a graphics processing unit (GPU) or both, processor cores, compute nodes, etc.), a main memory 1404 and a static memory 1406, which communicate with each other via a link 1408 (e.g., bus). The computer system 1400 may further include a video display unit 1410, an alphanumeric input device 1412 (e.g., a keyboard), and a user interface (UI) navigation device 1414 (e.g., a mouse). In one embodiment, the video display unit 1410, input device 1412 and UI navigation device 1414 are incorporated into a touch screen display. The computer system 1400 may additionally include a storage device 1416 (e.g., a drive unit), a signal generation device 1418 (e.g., a speaker), a network interface device 1420, and one or more sensors (not shown), such as a global positioning system (GPS) sensor, compass, accelerometer, or other sensor.

The storage device 1416 includes a machine-readable medium 1422 on which is stored one or more sets of data structures and instructions 1424 (e.g., software) embodying or utilized by any one or more of the methodologies or functions described herein. The instructions 1424 may also reside, completely or at least partially, within the main memory 1404, static memory 1406, and/or within the processor 1402 during execution thereof by the computer system 1400, with the main memory 1404, static memory 1406, and the processor 1402 also constituting machine-readable media.

While the machine-readable medium 1422 is illustrated in an example embodiment to be a single medium, the term "machine-readable medium" may include a single medium or multiple media (e.g., a centralized or distributed database, and/or associated caches and servers) that store the one or more instructions 1424. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1424 may further be transmitted or received over a communications network 1426 using a transmission medium via the network interface device 1420 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A method for programming a neuromodulator with a selected neuromodulation parameter set, the method comprising:
programming the neuromodulator with a schedule of different neuromodulation parameter sets to deliver sub-perception neuromodulation to a patient;
delivering sub-perception neuromodulation to a patient with the neuromodulator, using each of the different neuromodulation parameter sets in the schedule;
accessing, using a computerized system, a feedback input indicative of neuromodulation efficacy for each of the different neuromodulation parameter sets in the schedule;
ranking, using the computerized system and the feedback input, the neuromodulation efficacy for each of the different neuromodulation parameter sets in the schedule to provide evaluation results for the different neuromodulation parameter sets;
determining, using a machine learning algorithm of the computerized system, a revised schedule of neuromodulation parameter sets based on the evaluation results from at least one previous schedule, wherein the revised schedule differs from an immediately preceding schedule by including at least one different parameter set than was included in the immediately preceding schedule;
programming, using the computerized system, the neuromodulator with the revised schedule of neuromodulation parameter sets;
delivering sub-perception neuromodulation to the patient with the neuromodulator, using each of the different neuromodulation parameters sets in the revised schedule; and
iterating the accessing, the ranking, the determining, and the programming with adaptive learning until the evaluation results indicate that the selected neuromodulation parameter set was used to deliver sub-perception neuromodulation.

2. The method of claim 1, wherein the schedule includes:
a rotating or shifting schedule of parameter sets, or
a random cycling of a plurality of parameter sets.

3. The method of claim 1, wherein the feedback input includes a pain metric.

4. The method of claim 1, wherein the feedback input further includes a satisfaction evaluation, a self-reported activity, a visual analog scale, or a numerical rating scale.

5. The method of claim 1, further comprising receiving a user-provided search objective used to provide the evaluation results.

6. The method of claim 1, wherein the ranking the neuromodulation efficacy for each of the different neuromodulation parameter sets in the schedule to provide evaluation results includes sorting the neuromodulation efficacy for the different neuromodulation parameter sets.

7. The method of claim 1, the ranking the neuromodulation efficacy for each of the different neuromodulation parameter sets includes scoring each of the different neuromodulation parameter sets and discarding one or more parameter sets that fail to meet a threshold score.

8. The method of claim 1, wherein the different neuromodulation parameter sets include a first parameter set and a second parameter set, and the delivering sub-perception neuromodulation includes delivering the sub-perception neuromodulation using the first parameter set for at least a wash-in time, and initiating delivery of the sub-perception neuromodulation using the second parameter set at least after a wash-out time after the sub-perception neuromodulation using the first parameter set has terminated.

9. The method of claim 8, wherein the wash-in time or wash-out time is user-provided or is determined using the feedback input.

10. A non-transitory machine-readable medium including instructions, which when executed by a machine, cause the machine to perform a method for programming a neuromodulator with a selected neuromodulation parameter set, the method comprising:
programming the neuromodulator with a schedule of different neuromodulation parameter sets to deliver sub-perception neuromodulation to a patient, wherein the neuromodulator is configured to deliver sub-perception neuromodulation to a patient using each of the different neuromodulation parameter sets in the schedule;
accessing a feedback input indicative of neuromodulation efficacy for each of the different neuromodulation parameter sets in the schedule;
ranking, using the feedback input, the neuromodulation efficacy for each of the different neuromodulation parameter sets in the schedule to provide evaluation results for the different neuromodulation parameter sets;
determining, using a machine learning algorithm, a revised schedule of neuromodulation parameter sets based on the evaluation results from at least one previous schedule, wherein the revised schedule differs from an immediately preceding schedule by including at least one different parameter set than was included in the immediately preceding schedule;
programming the neuromodulator with the revised schedule of neuromodulation parameter sets, wherein the neuromodulator is configured to deliver sub-perception neuromodulation to the patient using each of the different neuromodulation parameters sets in the revised schedule; and
iterating the accessing, the ranking, the determining, and the programming with adaptive learning until the evaluation results indicate that the selected neuromodulation parameter set was used to deliver sub-perception neuromodulation.

11. The non-transitory machine-readable medium of claim 10, wherein the feedback input includes a pain metric.

12. The non-transitory machine-readable medium of claim 10, wherein the feedback input includes a satisfaction evaluation.

13. The non-transitory machine-readable medium of claim 10, wherein the feedback input includes a self-reported activity.

14. The non-transitory machine-readable medium of claim 10, wherein the feedback input includes a visual analog scale.

15. The non-transitory machine-readable medium of claim 10, wherein the feedback input includes a numerical rating scale.

16. The non-transitory machine-readable medium of claim 10, wherein the schedule includes:
a rotating or shifting schedule of parameter sets, or
a random cycling of a plurality of parameter sets.

17. A system comprising:
a neuromodulator; and
a programmer, including a processor and a memory device comprising instructions, which when executed by the processor, cause the processor to perform a method for programming the neuromodulator with a selected neuromodulation parameter set, the method comprising:
programming the neuromodulator with a schedule of different neuromodulation parameter sets to deliver sub-perception neuromodulation to a patient, wherein the neuromodulator is configured to deliver sub-perception neuromodulation to a patient using each of the different neuromodulation parameter sets in the schedule;
accessing a feedback input indicative of neuromodulation efficacy for each of the different neuromodulation parameter sets in the schedule;
ranking, using the feedback input, the neuromodulation efficacy for each of the different neuromodulation parameter sets in the schedule to provide evaluation results for the different neuromodulation parameter sets;
determining, using a machine learning algorithm, a revised schedule of neuromodulation parameter sets based on the evaluation results from at least one previous schedule, wherein the revised schedule differs from an immediately preceding schedule by including at least one different parameter set than was included in the immediately preceding schedule;
programming the neuromodulator with the revised schedule of neuromodulation parameter sets, wherein the neuromodulator is configured to deliver sub-perception neuromodulation to the patient using each of the different neuromodulation parameters sets in the revised schedule; and
iterating the accessing, the ranking, the determining, and the programming with adaptive learning until the evaluation results indicate that the selected neuromodulation parameter set was used to deliver sub-perception neuromodulation.

18. The system of claim 17, wherein the schedule includes:
a rotating or shifting schedule of parameter sets, or
a random cycling of a plurality of parameter sets.

19. The system method of claim 17, further comprising receiving a user-provided search objective used to provide the evaluation results.

20. The system of claim 17, wherein the different neuromodulation parameter sets include a first parameter set and a second parameter set, and the delivering sub-perception neuromodulation includes delivering the sub-perception neuromodulation using the first parameter set for at least a wash-in time, and initiating delivery of the sub-perception neuromodulation using the second parameter set at least after a wash-out time after the sub-perception neuromodulation using the first parameter set has terminated, wherein the wash-in time or wash-out time is user-provided or is determined using the feedback input.

* * * * *